United States Patent
Arkans et al.

(10) Patent No.: US 11,672,432 B2
(45) Date of Patent: Jun. 13, 2023

(54) APPARATUS AND METHODS OF SENSING A PATIENT CONDITION, SUCH AS ANATOMY POSITION, AND OF CONTROLLING PATIENT APPLICATIONS

(71) Applicant: GNOTRIX, LLC, San Marcos, CA (US)

(72) Inventors: Edward Arkans, Carlsbad, CA (US); Brian Lakin, Escondido, CA (US)

(73) Assignee: GNOTRIX, LLC, San Marcos, CA (US)

( * ) Notice: Subject to any disclaimer, the term of this patent is extended or adjusted under 35 U.S.C. 154(b) by 645 days.

(21) Appl. No.: 16/483,895

(22) PCT Filed: Feb. 4, 2018

(86) PCT No.: PCT/US2018/016771
§ 371 (c)(1),
(2) Date: Aug. 6, 2019

(87) PCT Pub. No.: WO2018/144963
PCT Pub. Date: Aug. 9, 2018

(65) Prior Publication Data
US 2020/0093383 A1 Mar. 26, 2020

Related U.S. Application Data

(60) Provisional application No. 62/455,512, filed on Feb. 6, 2017.

(51) Int. Cl.
*A61B 5/021* (2006.01)
*A61B 5/11* (2006.01)
*A61H 9/00* (2006.01)

(52) U.S. Cl.
CPC ........ *A61B 5/02141* (2013.01); *A61B 5/1116* (2013.01); *A61H 9/0078* (2013.01);
(Continued)

(58) Field of Classification Search
CPC .................... A61B 5/02141; A61B 5/1116
(Continued)

(56) References Cited

U.S. PATENT DOCUMENTS 9,889,038 B1 * 2/2018 Cahan .................. A61H 9/0085
10,517,489 B2 * 12/2019 Narasimhan ............. A61B 5/11
(Continued)

FOREIGN PATENT DOCUMENTS

EP 0465345 1/1992
EP 2436349 4/2012
(Continued)

OTHER PUBLICATIONS

Hollis, Ezrela, International Search Report, dated May 8, 2018, 9 pages, Australian Patent Office, PO Box 200, Woden ACT 2606, Australia.
(Continued)

*Primary Examiner* — Carl H Layno
*Assistant Examiner* — Manolis Pahakis
(74) *Attorney, Agent, or Firm* — Henricks Slavin LLP

(57) ABSTRACT

Patient therapy and patient condition sensing devices and methods can be operated as a function of estimated internal hydrostatic pressure of a body part, for example at a position where a pressure or compression therapy is applied. Information relating to a patient's position, posture, ambulation and/or a physiological condition such as blood pressure can be used to control pressure or compression therapy.

29 Claims, 9 Drawing Sheets

(52) U.S. Cl.
CPC .............. *A61H 2201/165* (2013.01); *A61H 2201/5071* (2013.01); *A61H 2201/5084* (2013.01); *A61H 2205/106* (2013.01); *A61H 2209/00* (2013.01); *A61H 2230/045* (2013.01); *A61H 2230/625* (2013.01)

(58) Field of Classification Search
USPC ........................................................ 600/490
See application file for complete search history.

(56) References Cited

U.S. PATENT DOCUMENTS

| | | | |
|---|---|---|---|
| 10,702,171 B2 * | 7/2020 | Narasimhan | A61B 5/022 |
| 10,779,738 B2 * | 9/2020 | Sullivan | A61B 5/6824 |
| 2004/0073123 A1 * | 4/2004 | Hessel | A61B 5/7221 |
| | | | 600/490 |
| 2005/0080345 A1 * | 4/2005 | Finburgh | A61B 5/681 |
| | | | 600/501 |
| 2006/0079792 A1 * | 4/2006 | Finburgh | A61B 5/681 |
| | | | 600/503 |
| 2008/0033307 A1 * | 2/2008 | Baudoin | A61B 5/02225 |
| | | | 600/490 |
| 2010/0324429 A1 | 12/2010 | Leschinsky | |
| 2011/0196269 A1 | 8/2011 | Arkans | |
| 2012/0083712 A1 | 4/2012 | Watson et al. | |
| 2012/0265240 A1 | 10/2012 | Ganske et al. | |
| 2012/0277636 A1 | 11/2012 | Blondheim et al. | |
| 2012/0277789 A1 | 11/2012 | Caldarone et al. | |
| 2014/0257156 A1 * | 9/2014 | Capra | A43C 11/165 |
| | | | 602/5 |
| 2014/0303460 A1 | 10/2014 | Corley et al. | |
| 2015/0327784 A1 * | 11/2015 | Lading | A61B 5/7282 |
| | | | 600/485 |
| 2015/0366565 A1 | 12/2015 | Shaltis et al. | |
| 2016/0051176 A1 * | 2/2016 | Ramos | G01F 23/265 |
| | | | 600/573 |
| 2016/0089036 A1 | 3/2016 | Kobayashi et al. | |
| 2016/0100793 A1 | 4/2016 | Barak | |
| 2016/0120418 A1 * | 5/2016 | Oksala | A61B 5/0205 |
| | | | 600/483 |
| 2016/0166463 A1 | 6/2016 | Douglas et al. | |
| 2016/0175184 A1 | 6/2016 | Arkans et al. | |
| 2016/0220808 A1 * | 8/2016 | Hyde | A61B 5/6895 |
| 2017/0209053 A1 * | 7/2017 | Pantelopoulos | A61B 5/7264 |
| 2017/0312165 A1 * | 11/2017 | Johnson | A61B 5/021 |
| 2017/0340209 A1 * | 11/2017 | Klaassen | A61B 5/021 |
| 2017/0360313 A1 * | 12/2017 | Baek | A61B 5/681 |
| 2019/0059752 A1 * | 2/2019 | Botsva | A61B 5/332 |

FOREIGN PATENT DOCUMENTS

| | | |
|---|---|---|
| EP | 2964164 | 5/2020 |
| JP | 4-64334 | 2/1992 |
| JP | 2006-102190 | 4/2004 |
| JP | 2012-71136 | 4/2012 |
| KR | 20110050000 | 5/2011 |
| WO | WO 1998/056321 | 12/1998 |
| WO | WO 1998/056331 | 12/1998 |
| WO | WO 2016/040256 | 3/2016 |
| WO | WO 2016/055992 | 4/2016 |
| WO | WO 2016/073777 | 5/2016 |

OTHER PUBLICATIONS

Hollis, Ezrela, Written Opinion of the International Searching Authority, dated Mar. 8, 2018, 10 pages, Australian Patent Office, PO Box 200, Woden ACT 2606, Australia.

Shmonin, Vladimir, European Search Report, dated Oct. 13, 2020, 10 pages, European Patent Office, Munich, Germany.

Singh, Subhash, Examination Report, dated Jan. 5, 2022, 6 pages, Intellectual Property India, New Delhi, India.

Onoda, Tatsushi, Office Action, dated Jul. 13, 2022, 6 pages (Translation), Japan Patent Office, Tokyo, Japan.

* cited by examiner

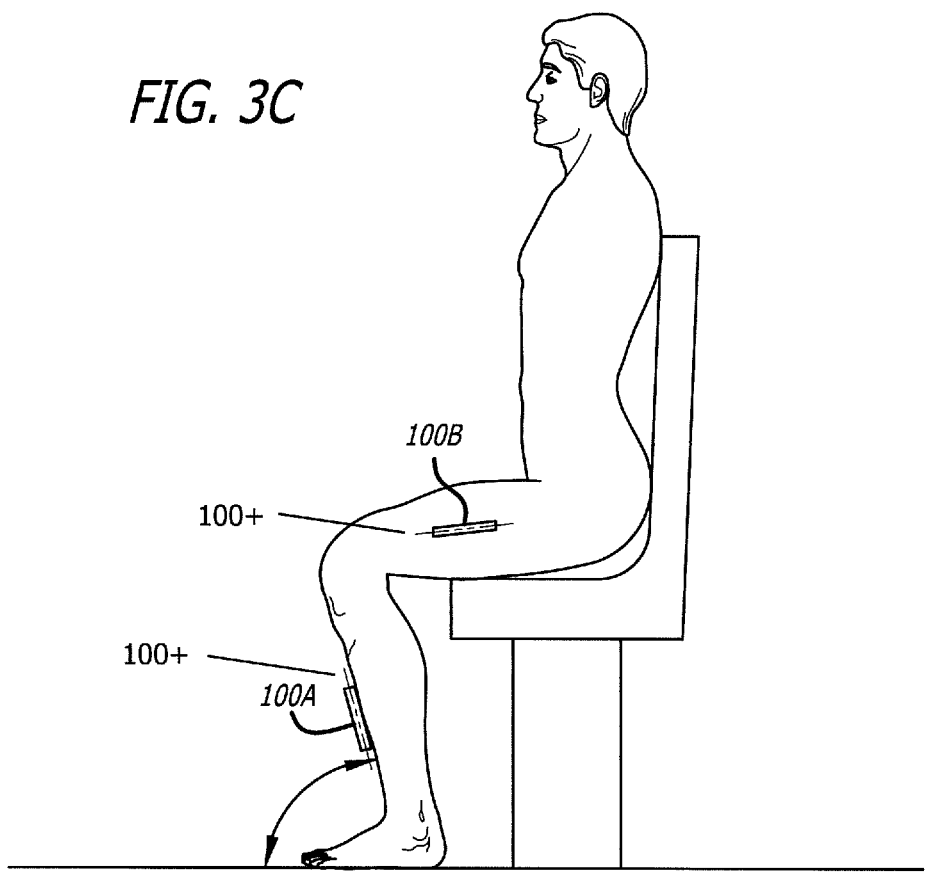

APPARATUS AND METHODS OF SENSING A PATIENT CONDITION, SUCH AS ANATOMY POSITION, AND OF CONTROLLING PATIENT APPLICATIONS

CROSS REFERENCE TO RELATED APPLICATIONS

This application is a National Stage of International Application No. PCT/US18/16771, filed Feb. 4, 2018, which claims priority from U.S. 62/455,512 filed Feb. 6, 2017, the entire contents of which are incorporated herein by reference.

BACKGROUND

Field

These inventions relate to apparatus and methods for sensing anatomy positions or physiological conditions, and/or using information relating to anatomy positions and/or physiological conditions for controlling or applying patient applications such as therapies or the like, including using an accelerometer, magnetometer, or other position or motion sensors to sense a position, posture or motion of a patient and/or using such information to apply, affect or change a therapy, for example pressure or compression therapy.

SUMMARY

Apparatus and methods are described for applying and/or changing a pressure or compression therapy as a function of a sensed patient condition. For example, apparatus and methods are described for applying and/or changing an applied pressure or a compression therapy as a function of position or posture, including ambulation, a patient physiological condition, for example blood pressure, or other patient conditions. Any one or more of the sensing and therapy functions described herein can be carried out concurrently, simultaneously, sequentially, seriatim, and/or at least during a single therapy session. A therapy session might be an hour or two or less.

Furthermore, apparatus and methods are described for applying and/or changing a pressure or compression therapy, for example, as a function of a patient's internal hydrostatic pressure, including as a function of a patient's limb internal hydrostatic pressure (IHP) estimation for example, within the vasculature, and for example at or near a location at which therapy is being or will be applied. As used herein, patient position includes a patient's posture, including ambulation, and as used herein, patient condition includes patient position and a patient's posture, and also a patient's physiological condition or status.

The apparatus and methods may carry out the application or the changing of pressure or of compression therapy automatically, for example based on stored algorithms or information. The apparatus and methods may function based on information about or estimates of internal hydrostatic pressure (IHP) of one or more of the body's vasculature, namely the arteries, veins and lymphatic system at a selected body location. While several examples are described herein of acting on the body's vasculature, it should be understood that the apparatus and methods described herein apply to any of the elements of the body's vasculature, which includes arteries, arterioles, veins, venules, capillaries and all lymphatic vessels and structures including nodes.

Apparatus for sensing a patient condition may include sensors for sensing patient position or posture including ambulation, including sensors for sensing position or posture including ambulation and/or changes in position or posture including ambulation of a patient's limb and/or torso, for example temporal changes. Changes in position and/or posture referenced herein also include changes arising from ambulation or other translational movements or motions. Apparatus may include devices for receiving information representing patient condition, including position or posture including ambulation and/or changes in position or posture including ambulation of a patient's anatomy and for deriving information about an internal hydrostatic pressure of a portion of a patient's anatomy. Information can be derived, for example, by calculating, compiling and/or acquiring information and processing such information to provide an estimate or evaluation for an internal hydrostatic pressure. Additionally or alternatively, apparatus may include pressure or compression therapy apparatus receiving information about, or having sensors for sensing, patient position or posture including ambulation, including sensors for sensing position or posture including ambulation and/or changes in position or posture including ambulation, or that may be configured for being controlled by apparatus as a function of information determined about an internal hydrostatic pressure of a portion of a patient's anatomy, for example an anatomy portion at or near application of pressure or compression for therapy.

In one example of apparatus and methods described herein, apparatus uses position sensors that estimate a position or positions of one or more body parts to obtain information about the patient condition, for example position, posture, ambulation or physiologic condition. The apparatus and methods can use the information for estimating or approximating a patient's internal hydrostatic pressure, for example internal hydrostatic pressure at a selected anatomic location. Such apparatus may be separate from or may be integral with the apparatus for applying the pressure or compression therapy. For example, such apparatus and methods may use position sensors that estimate a position or posture including ambulation or positions of one or more body parts for estimating or approximating a patient's internal hydrostatic pressure for applying or adjusting pressure or compression therapy. In one example, position sensors estimate the position or positions of one or more body parts relative to gravity, and the position or positions of one or more body parts may be used to estimate or approximate a value of an internal hydrostatic pressure of the respective body part. One or more microprocessors can be used to estimate or approximate a value of an internal hydrostatic pressure, and can be used to provide controls for controlling application of therapy, for example application of pressure or compression therapy. Application of pressure or compression therapy may be carried out as a function of the estimated internal hydrostatic pressure of the respective body part.

In other examples of apparatus and methods described herein, apparatus uses sensors to obtain information about the patient's physiological condition, for example taking a physiological measurement (for example, blood pressure, ankle pressure, metatarsal pressure, toe pressure, blood pressure under a bladder or cuff, or determining an ankle brachial index), and if desired may also use such information in conjunction with information about the patient's position, posture or motion condition. The apparatus and methods can use the sensed information about a physiological and/or position condition, and if desired along with any static information, for example anatomical measurements such as height, sex, weight and/or distance measurements, for adjusting a therapy, for example pressure or compression therapy, and one or more devices can be used to control application of therapy, for example application of pressure or compression therapy. Application of pressure or compression therapy may be carried out as a function of the sensed patient condition, for example to adjust a baseline pressure or pressures, or default pressures or any of the other actions described herein.

In any of the examples of apparatus and methods described herein, the apparatus and methods for sensing a patient condition (physiological and/or positional) and the apparatus and methods for applying a therapy can be used in conjunction with each other, can be carried out with integrated apparatus or otherwise combined. In one example, an assembly of a pressure sensor combined with a therapy structure can be placed on a patient's limb and a pressure at the location of the assembly can be sensed, for example a blood pressure, a compression pressure or a brachial pressure or brachial index. In another example, a position sensor combined with a therapy structure can be placed on a patient's limb and the position of the limb at the location of the assembly can be sensed, for example horizontal or perpendicular to the gravitational field, vertical or parallel to the gravitational field, at an angle to the gravitational field, or moving in the gravitational field over a selected period of time. In a further example, a position sensor and/or a physiological sensor combined with a therapy structure can be placed on a patient's limb or at multiple locations and patient conditions sensed in accordance with the sensing structures. The information sensed in these examples can then be used to apply therapy to the patient, for example by setting therapy pressures, for example initially and/or over the therapy session, or by changing existing settings such as defaults. The applying of therapy to the patient, for example by setting therapy pressures, for example initially and/or over the therapy session, or by changing existing settings such as defaults can be done in real time with the sensing.

In any of the examples described herein, patient condition sensors for sensing patient position or posture including ambulation may include one or more of accelerometers, magnetometers, gyroscopes, inclination sensors, tilt sensors, other motion detecting sensors, goniometers, flex sensors, or similar sensors. Such sensors can be used to provide data for estimating a patient's position or posture including ambulation or change in position or posture including ambulation, which can be used to provide a value or values estimating or approximating an internal hydrostatic pressure for a portion or portions of a patient's anatomy. Therapies may then be applied as a function of the estimated internal hydrostatic pressure. For example, pressure or compression therapies, for example for conditions identified herein (for example deep vein thrombosis, etc.), can be configured or adjusted as a function of the patient's condition, including one or more of a physiological measurement, position or posture including ambulation or change in position or posture including ambulation, as a function of values representing estimates of a patient's physiological condition, position or posture including ambulation or change in physiological condition, position or posture including ambulation, and/or as a function of values representing estimates of internal hydrostatic pressures for a portion or portions of a patient's anatomy as sensed by one or more desired sensors.

In one example, pressure or compression therapy can be applied to a limb according to a first pressure profile when the patient is supine, a second pressure profile if the patient is sitting, a third pressure profile if the patient is reclining, a fourth pressure profile if the patient is standing, a fifth pressure profile if the patient is ambulating or walking, a sixth pressure profile when the patient's limb is elevated, and so on. In the foregoing examples, the first pressure profile may have a lower pressure maximum than in the second through fourth pressure profiles, while the fifth pressure profile may use the fourth pressure profile or have a different or lower pressure maximum than in the first through fourth pressure profiles and may even be set at baseline, for example where the therapy is for prevention of DVT or when the limb is elevated. An applied therapy can then be adjusted as discussed herein when the patient physiological condition, position or posture, including ambulation, changes, for example between ambulation, standing, sitting, reclining and lying down. For example, when applying compression therapy to prevent deep vein thrombosis (DVT), cyclical compression may be halted during ambulation or only provided as a static compression. This static compression may allow overall static and dynamic pressures applied to a limb to increase due to muscle contractions. If the patient changes posture from supine to sitting positions, the applied pressures may be increased to account for the increased IHP.

In another example, when applying compression therapy for chronic venous insufficiency (CVI), the amount of applied pressure may be increased when the patient changes posture from supine to sitting positions and increased further as the patient moves from sitting to standing positions. During ambulation static and dynamic pressures applied to a limb may be allowed to increase due to muscle contractions, allowed to increase for example by not lowering or changing downward a preceding pressure profile. These increased pressures, or pressure peaks in the dynamic case, will serve to improve the limb's ability to more efficiently and more completely empty its vasculature, including veins, venules, capillaries and lymphatic components. As the patient moves from standing to sitting and sitting to supine or semi-reclined positions, the applied pressures may be reduced with reduced IHPs as sensed or estimated. Applied therapies may be different depending on the condition being treated, for example those discussed herein, and/or depending on the anatomical location being treated. Variations in pressure profiles may also be applied as a function of patient characteristics, such as height, weight, or the like.

In a simple form, a form of the apparatus can operate without user input. For example, the device can rely on default value settings such as the values of applied pressures for various patient positions or postures detected before or during operation of the apparatus. Also, IHP default values can be set based on the intended limb location of the device applying therapy (thigh or calf, for example), such as where the apparatus will be dedicated for use only with therapy application at that location. Alternatively a connection configuration of the therapy device can be keyed or have a unique code for telling the apparatus where the therapy application device will be located, such as where the therapy device is configured for application to a single limb location. Connection at one location can be keyed differently from a connection at another location. In other configurations, the apparatus can apply therapy based on default settings combined with data about the individual or can apply therapy based on such individual data without using default settings. For example, the apparatus can apply therapy based in whole or in part upon average anthropometric data for such things as the relationship between patient height and the distance from the right atrium to the bottom or plantar surface of the foot. Default pressure values for various therapies may be based upon those commonly used in current practice and then changed based on changes in the estimated IHP during a therapy session. For example, for treating CVI, the device may apply 25 mmHg in the supine patient at a location on the patient's calf as would a typical elastic stocking. As the device estimates that the patient has moved to a sitting position, the device may default to apply an additional 30 mmHg (for a total of 55 mmHg) to account for the increased IHP expected with the average person's height as related to the vertical right atrium (RA) to calf distance in a sitting position. Similarly, as the patient moves from a sitting to a standing position, the device may default to apply an additional 15 mmHg (for a total of 70 mmHg) to account for the increased IHP expected using similar anthropometric data as above. Likewise in the opposite direction for changes that can be made if the patient moves from standing, to sitting and/or to a supine position, or other position or posture or ambulation changes.

In another example, for treating CVI, the device may apply 20 mmHg in the supine patient at a location on the patient's calf as would a typical elastic stocking. As the device estimates that the patient has moved to a sitting position, the device may default to apply an additional 15 mmHg (for a total of 35 mmHg) to account for the increased IHP expected with the average person's height as related to the vertical right atrium (RA) to calf distance in a sitting position. Similarly, as the patient moves from a sitting to a standing position, the device may default to apply an additional 20 mmHg (for a total of 55 mmHg) to account for the increased IHP expected using similar anthropometric data as above. As the patient moves into a position where the limb is in an elevated position, the device may apply pressures lower than that of the default supine position. Since the angle of the limb relative to the ground, theta, can be measured and calculated by using an internal accelerometer, the applied pressure may be a function of theta and the supine default pressure. For example, the default supine pressure may be reduced by multiplying it by a constant (C) and multiplying by the sine of theta: Pressure at elevation= (sin(theta))×(C)×(supine default pressure). The magnitude of the angle theta can be determined from one or more sensing devices, for example on the calf, on the side, or both.

Additional examples of pressure profiles that can be used in apparatus such as that described herein are shown in the Table 1 below wherein a device user may select from a group of pressure settings shown in units of mmHg, the example being for a calf cuff. Values can also be provided for other cuff locations, for example a thigh cuff, arm cuff, and the like, for example in a table, as an algorithm or otherwise. Such settings may be referred to as "light" or "strong" or "arterial" or other terms that indicate the relative magnitude of programmed applied pressure ranges for various patient positions shown in the left most column. The "arterial" setting is for patient limbs with venous or lymphatic insufficiencies that may also have arterial occlusive disease and in whom larger applied pressures may be less desirable due to restriction of arterial blood flow to the limb or part of the limb. The "arterial" setting may also be used by the device automatically or under program control in conjunction with other sensing functions that may be used to indicate venous or lymphatic insufficiencies present or occurring with arterial occlusive disease, for example. For example, blood pressure or similar measurements of patient physiological conditions may indicate venous or lymphatic insufficiencies present or occurring with arterial occlusive disease, and such measurements or indications of physiological conditions may lead to changes or adjustments in the pressure settings for the pressure therapy or compression therapy device.

In the "arterial" setting, there may be a fixed set of pressure profiles or a lookup table or an algorithm available to select a suitable pressure profile. Alternatively, the device may accept pressure inputs from a user or clinician for one or more of the postural positions in the Table 1 below. Alternatively, the device may accept a measured physiological parameter and then use an algorithm to determine pressures for one or more of the postural positions. Physiological parameters that may be used include arterial ankle or toe pressures, such as systolic or mean pressures, or arterial pressures measured at the level of intended compression such as at the level of a venous stasis ulcer or at the level of the edematous tissues to be compressed by the device. Other possible measured physiological parameters are the ankle/brachial index (ABI) or the toe/brachial index (TBI). Generally, in the case of a patient with arterial disease, for example, the default pressure profiles within the device would be reduced in relation to the increased severity of the arterial disease. The smaller the arterial indexes (ABI or TBI), the more the default pressure profiles would be reduced in pressure. Similarly, the lower the pressures measured such as the toe pressure (TP) or ankle pressure (AP), the more the default pressure profiles would be reduced in pressure One possible algorithm would reduce a default pressure profile such as the "light" profile, by the measured ABI or TBI. For example, if the "light" pressure profile stored in the device had default values for a calf cuff, in mmHg, of 25 supine, 40 sitting, 60 standing, 10 with limb elevation and the ABI was 0.5, then a new pressure profile would be calculated to be 12.5, 20, 30 and 5 respectively. Another possible algorithm uses the measured pressure for example TP or in another example an AP, in mmHg, as an input to the device. TPs below 70 would reduce a pressure profile with lower TPs resulting in lower pressure profiles.

TABLE 1

|  | Light (mmHg) | Strong (mmHg) | Arterial (mmHg) |
|---|---|---|---|
| Supine | 20 to 30 | 30 to 40 | 0 to 10 |
| Sitting | 35 to 45 | 45 to 55 | 25 to 35 |
| Standing | 55 to 65 | 65 to 70 | 35 to 45 |
| Ambulation | 65 with peaks to 80 | 70 with peaks to 90 | 45 with peaks to 60 |
| Limb elevated | 0 to 20 | 10 to 30 | 0 to 10 |

In other configurations alternatively or additionally, certain data may be entered manually into apparatus such as that described herein, such as the individual's height or a distance from RA to point of interest of the leg such as the mid-calf or a malleolus. Also or alternatively, data such as pressure increases between supine and sitting or standing may be manually entered rather than using average anthropometric data. Since men and women have different average anthropometric values, the sex of the patient may also be entered into the device to provide additional accuracy of estimated height and weight. For pressure offloading configurations, the device can default to or assume an average body weight, or such things as gender or known body weight can be manually entered for better accuracy.

In another configuration the measured distance from the RA to the top of the head and the measured distance from the sole of the foot to the point of interest for application of therapy can be entered such that the device may then calculate the vertical distance from RA to point of interest by subtracting the two measurements from the patient's height in order to obtain a more accurate IHP estimation.

In other configurations, device timing data can be set as default values or entered manually into apparatus such as that described herein. In the case of cyclically applied pressures as for prevention of DVT or for treatment of lymphedema, in addition or alternative to pressure data as previously described, timing data can be handled similarly. Cyclical pressure values may be set as default values or manually entered. Static pressure values that are applied in DVT, CVI and Lymphedema configurations when the device detects ambulation may be set as default or manually entered, for example as shown in the above Table 1.

Timing values such as latency periods may be set by default or manually entered. Examples of such latency periods include time between dynamic pressure pulses, time after detection of postural changes before application of a dynamic pressure pulse, time after detection of ambulation or muscle activity before application of a dynamic pressure pulse, etc.

In another configuration the device may include electronics capable of recording and/or displaying the average daily usage of the device or other recorded usage information or measurements such that a clinician or other observer may assess the compliance of the user or so-called "patient compliance", including for example time of day, duration, and similar data. The device may also record the durations of times that the user has spent in the various detected positions including ambulation. In the case of ambulation other parameters including time of day, duration, and/or walking pace may also be recorded for later display or output thereby providing an indication of the user's sedentary or exercise habits.

In another example of a system, a user may use a smart phone application to either accept the various default values or manually select them. The smart phone may communicate with the devices wirelessly to exchange data. A smart phone may also communicate with an internet server or directly to another device such as to a clinician's mobile phone or computer to provide information regarding the patient's usage such as date and time of use, device settings, etc., and for the clinician to modify data settings.

Apparatus as described herein can be used to apply or adjust settings in a therapy apparatus as a function of a patient condition, for example patient position or posture, including ambulation, as a function of data representing a patient position or posture, including ambulation, as a function of data representing an internal hydrostatic pressure of a patient, for example such as may be obtained from such apparatus, and/or as a function of data representing a patient physiologic condition, for example blood pressure. For example, pressure or compression therapy can be changed by decreasing or increasing a maximum pressure for a pressure profile if the patient is ambulating, or by decreasing or increasing a maximum pressure for a pressure profile if the patient is standing without otherwise moving. In another example, pressure or compression therapy can be changed by decreasing or increasing a baseline pressure for a pressure profile if the patient is or is not ambulating, for example to account for muscle geometry changes from muscle contraction. Pressure or compression therapy can be changed dynamically based on real-time or accumulated position or posture including ambulation changes sensed by position or posture, including ambulation, sensors, for example. For example, time variation of position sensors can be used to apply pressure to a body part as a function of estimated activity.

As used herein, position sensors, sensing position or posture, including sensing ambulation, and sensing position or posture or ambulation of a patient's anatomy includes sensors for and changes in such position or posture, including ambulation.

These and other examples are set forth more fully below in conjunction with drawings, a brief description of which follows.

BRIEF DESCRIPTION OF THE DRAWINGS

FIG. 3C is a further side elevation view of a user showing the lower legs forming a non-90 degree angle to the floor.

DETAILED DESCRIPTION

Figure 1:
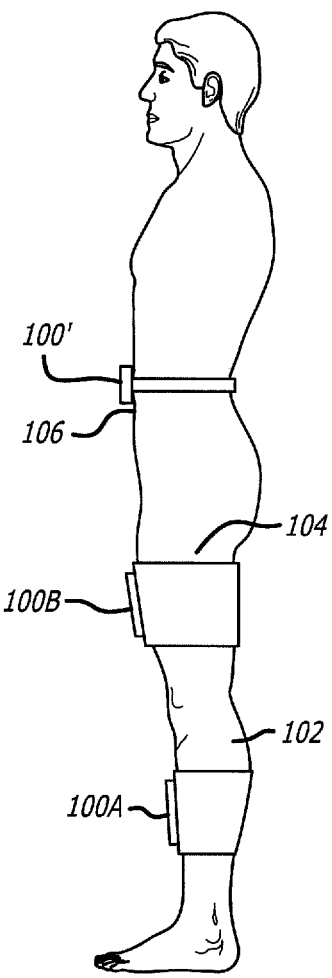
FIG. 1 is a side elevation view of a user, for example a patient, of the apparatus and methods described herein having a plurality of sensing apparatus and a plurality of devices for applying therapy.

This specification taken in conjunction with the drawings sets forth examples of apparatus and methods incorporating one or more aspects of the present inventions in such a manner that any person skilled in the art can make and use the inventions. The examples provide the best modes contemplated for carrying out the inventions, although it should be understood that various modifications can be accomplished within the parameters of the present inventions.

Examples of patient condition sensing devices, including sensing devices such as physiological measuring devices and position devices, and of therapy devices, and of methods of making and using the patient condition sensing devices and therapy devices are described. Examples of assemblies of patient condition sensing devices as described herein and therapy devices and of methods of making and using the assemblies are also described. Depending on what feature or features are incorporated in a given structure or a given method, benefits can be achieved in the structure or the method. For example, patient condition sensing devices in the form of, for example, position devices using any one or more of accelerometers, magnetometers, inclinations sensors, tilt sensors, motion sensors, goniometers, or the like, may be used to more reliably identify a patient's condition, for example position or posture, including ambulation, adjust treatment modalities, estimate internal hydrostatic pressure, and/or permit more flexible treatment for a patient's condition. One or more of such position devices can also help in conserving energy, such as battery life, which may also permit more flexible treatment for a patient's condition. Patient condition sensing devices in the form of, for example, physiological measuring devices may also be used to more reliably identify a patient's condition, and used to adjust a treatment or treatments. Additionally or alternatively, therapy devices and/or methods can be adjusted using information about a patient's condition, for example position, posture, ambulation and/or physiological state to more desirably apply therapy to the patient.

These and other benefits will become more apparent with consideration of the description of the examples herein. However, it should be understood that not all of the benefits or features discussed with respect to a particular example must be incorporated into a device, component, assembly or method in order to achieve one or more benefits contemplated by these examples. Additionally, it should be understood that features of the examples can be incorporated into a device, component, assembly or method to achieve some measure of a given benefit even though the benefit may not be optimal compared to other possible configurations. For example, one or more benefits may not be optimized for a given configuration in order to achieve cost reductions, efficiencies or for other reasons known to the person settling on a particular product configuration or method.

Examples of a number of patient condition sensing device configurations and of therapy device configurations and of methods of making and using the patient condition sensing devices and therapy devices are described herein, and some have particular benefits in being used together. However, even though these apparatus and methods are considered together at this point, there is no requirement that they be combined, used together, or that one component, assembly or method be used with any other component, assembly or method, or combination. Additionally, it will be understood that a given component, assembly or method could be combined with other structures or methods not expressly discussed herein while still achieving desirable results.

Accelerometers are used as examples of a patient condition sensing device that can be used, used in conjunction with and/or incorporated into one or more of the treatment devices described herein, providing features and one or more of the benefits described herein, and in particular used with or in pressure and/or compression applications for patients' limbs, for example. Patients are not always undergoing treatments in only a single position or posture, including ambulation, and descriptions of patient condition sensors in the form of position devices herein include treatment modalities applied to a patient's leg in several configurations. While those several modalities and limb configurations are described herein as examples, patient condition sensing devices used in other treatment modalities and for other patient positions or postures or modes of ambulation can benefit from one or more of the present inventions.

As used herein, "substantially" shall mean the designated parameter or configuration, plus or minus 10%. However, it should be understood that terminology used for orientation or relative position, such as front, rear, side, left and right, upper and lower, and the like, may be used in the Detailed Description for ease of understanding and reference, and may not be used as exclusive terms for the structures being described and illustrated.

Apparatus for using patient condition sensing devices, for example position sensors, and pressure or compression therapy devices using estimates or approximations of internal hydrostatic pressure can take a number of configurations. For example, such apparatus can be individual modules of any of the devices described herein, for example that can communicate with one or more others of the individual modules of any of the devices described herein, or such apparatus can be combinations of components, for example combinations of patient condition sensing devices, for example position sensors, and pressure or compression therapy devices in an integrated unit. In the examples illustrated herein, at least one and several of the examples contemplate integrated units, but it is understood that an integrated unit can also be implemented in one or more of a plurality of individual units, as desired, and used in those forms.

Figure 6:
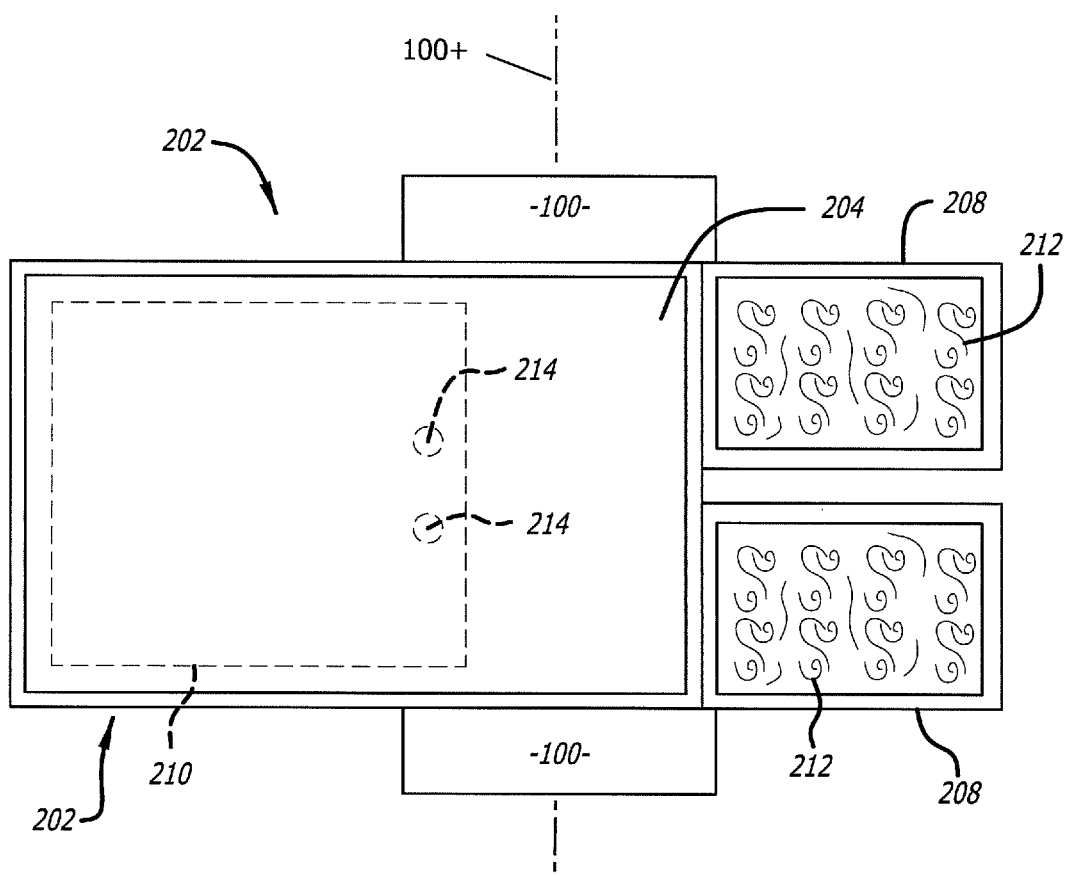
FIG. 6 is a schematic and plan view of a pressure application device in the form of a pressure cuff, and which also has a sensor and/or control unit.
Figure 7:
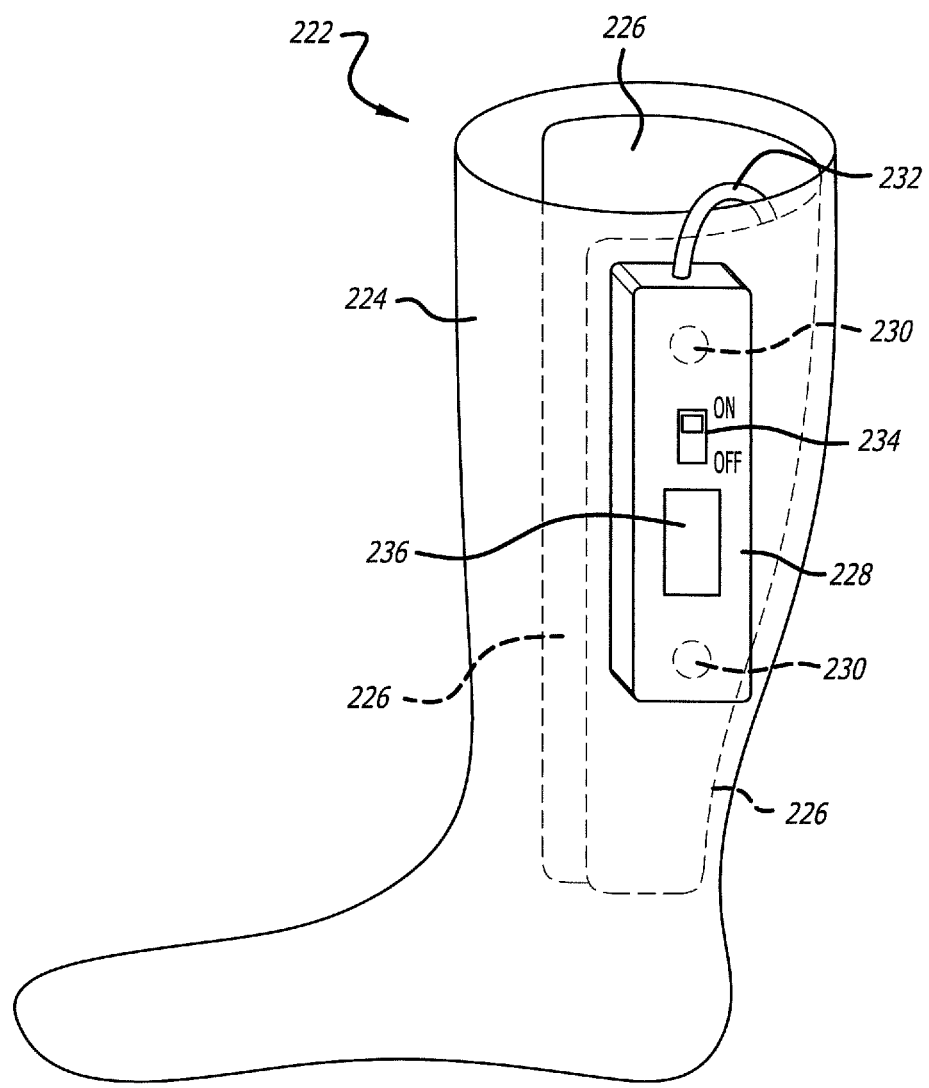
FIG. 7 is a schematic and side elevation view of an elastic compression stocking in combination with a pressure bladder and a sensor and/or control unit.

One example of apparatus for sensing a patient's condition, for example position or posture, which may include ambulation, and applying a pressure or a therapy (FIGS. 1 and 2) may be housed in one or more assemblies 100, each of which assemblies (FIG. 2) may communicate directly, or indirectly through a processor or other device, with one or more pressure or therapy devices, in the present example pressure applying bladder(s) 200. The bladders can be used to apply localized pressure, for example pressure to a surface of a limb, or compression, for example compression of a limb. The bladders 200 may take a number of configurations, and may be standalone devices or may be integrated with the assemblies 100. Integrated assemblies are illustrated in FIGS. 6-7. Pressure or therapy devices may be wired to apparatus for sensing the patient's condition, or may be wirelessly coupled to apparatus for sensing the patient's condition. Any pressure or therapy device may be wired or wirelessly coupled to a single or to multiple sensing apparatus, and each sensing apparatus in a group of sensing apparatus may be identical to each of the others or may be different from one or more of the others. A sensing apparatus may be any of the devices described herein. Additionally, pressure or therapy devices may be any of those described herein.

An assembly or assemblies 100 may be positioned at a number of locations on a patient's body, which positions may be determined based on one or more criteria. In one example, the criteria may be the body part to which therapy, for example pressure or compression therapy, is to be applied, and in another example the criteria may be the body part the condition, for example position, posture or ambulation, or physiological condition of which is to be sensed and evaluated, and in still another example the criteria may be both the body part for which the position is to be sensed and to which therapy is applied. Other criteria may be used alternatively or additionally.

Figure 2:
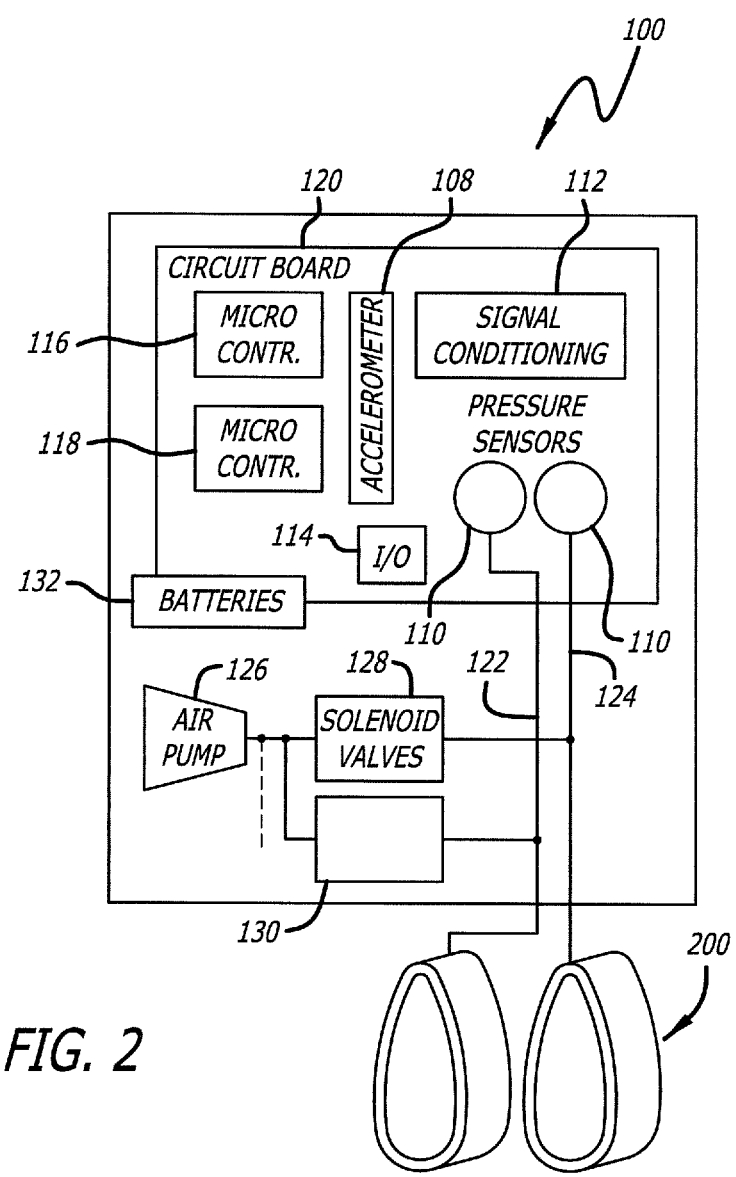
FIG. 2 is a schematic representation of an assembly and therapy devices, wherein the assembly includes components for operating the therapy devices and components for obtaining and/or processing information relating to the user's position or posture including ambulation for the parts of the anatomy associated with a respective assembly, for example a limb.

In one example of sensing apparatus, therapy apparatus and an assembly of sensing and therapy apparatus, illustrated in FIG. 1, each device can be used separately with the structures and functions described herein, independent of the other discrete devices on the patient or omitting one or both of the other discrete devices. In the present example, a first patient condition sensing apparatus is included, for example in a first assembly 100A applied to a patient's calf 102 and the patient condition sensing device and apparatus can be used for applying or causing to be applied a pressure and/or compression therapy to the calf according to a pressure profile, with the help of a bladder and wrap or other securement such as those described herein with which the assembly 100A (or 100B, 100C, and/or 100D) is associated. In one example, the pressure profile or other therapy routine is determined in part based on the patient condition as sensed by a sensor associated with the first assembly 100A, for example a position or posture of the calf or possible ambulation as sensed by a position sensor in the assembly 100A. Using only the first sensing apparatus such as that in the assembly 100A can form a complete sensing system that can be used for providing input to therapy apparatus, for setting or adjusting a therapy routine for the patient. In another example, as illustrated in FIG. 1, a second patient condition sensing apparatus is further included, for example in a second assembly 100B applied to a patient's thigh 104 for applying or causing to be applied a pressure and/or compression therapy to the thigh according to a pressure profile. In one example, the pressure profile applied to the thigh is determined in part based on the patient condition as sensed by a sensor associated with the second assembly 100B, for example a position or posture of the thigh or possible ambulation as sensed by a position sensor in the assembly 100B. The assembly 100B and components and functions can be identical to those of assembly 100A, or in other examples not illustrated, it can have fewer components and functions. Using the first and second assemblies 100A and 100B and their components and functions can form a complete sensing system that can be used for providing input to therapy apparatus, for setting or adjusting a therapy routine for the patient. In the example illustrated in FIG. 1, a further patient condition sensing apparatus is included, for example in a further assembly 100' secured at another body location, in the present example around the patient's abdomen 106, and includes a patient condition sensor associated with the assembly 100'. The information from the sensor can be used to provide input to therapy apparatus, for setting or adjusting a therapy routine for the patient, for example as a function of position or posture, or a possible indication of ambulation. In the example illustrated in FIG. 1, pressure profiles applied to the calf and/or to the thigh may be applied as a function of position or posture, including ambulation, information obtained from position sensors in the assemblies 100A, 100B and/or 100'. It is also understood that any one or more of the first, second and/or further patient condition sensors, positioned as illustrated and described or at other locations on the body, can be used for setting or adjusting a therapy routine for the patient to be applied at any location on the body, either alternative or additional to therapy applied at a location of a given patient condition sensor. For example, a given patient condition sensor can connect, send, transmit or make available to another device information relating to the patient condition, which information can then be used to apply a therapy at a location determined by the other device, which may include applying a therapy at the location of the other device or at the location of the sensor, or elsewhere.

An illustrative assembly 100 (FIG. 2) contains components for fixing and aligning each assembly and, if desired, a bladder to a body part, sensors such as accelerometers 108 and if desired pressure sensors 110, electronic circuitry 112 for signal conditioning of the sensors' outputs, and communication or input/output 114 between the various sensors and/or therapy devices, such as those associated with the assemblies 100 using wireless or wired communication protocols. Other sensors than accelerometers can be included additional or alternative to the accelerometer 108. One or more microcontrollers 116 and 118 can receive input for example from the user, and from the accelerometer and pressure sensors. One or more of the microcontrollers can store and process data using tables or algorithms stored in association with the microcontrollers, and can control various components for applying therapy, for example pressure or compression therapy. The electronics can be on one or more circuit boards 120. The electronics can be contained within the assembly 100, and may contain as few electronics as desired to achieve the desired purpose for the assembly. For example, an assembly can include control electronics and communications and/or input-output components for receiving data and for transmitting instructions to an adjacent therapy device and/or to other devices or assemblies for applying therapy. Additionally or alternatively, an assembly can include one or more sensors and communications components for communicating information developed in the sensors to other devices, including assemblies as described, or to a bladder or other therapy application device, which may be integrated with the assembly or separate, and either electronically and/or fluidically connected to the assembly or in remote communication with the assembly. Additionally or alternatively, a patient condition sensing device, such as the described assemblies can include communications and/or input-output components for receiving instruction data and for controlling therapy devices for applying therapy to a body part, for example through bladders or other pressure or compression components, for example based on instructions or data from other assemblies or devices. In the illustrated configuration of the assembly 100 device for sensing a patient condition shown in FIG. 2, the assembly includes the circuit board 120 secured in the assembly containing the one or more microcontrollers 116 and 118 (or suitable digital, analog and combinational circuitry for control of the operation of the apparatus), the signal conditioning component 112 and communications or input-output components 114, all of which are coupled together as necessary as would be understood by one skilled in the art. The accelerometer 108 would be secured in the assembly 100 in the desired position and orientation according to a reference associated with an assembly, such as a reference mark, alignment marker, shape indicator, or some other way of orienting the assembly so that the accelerometer position and orientation are known, represented in the present illustrations at 100+. The pressure sensors 110 are also included within the assembly 100 and coupled to the fluid lines 122 and 124, respectively, configured to sense the respective pressures in the fluid lines or developed in the respective bladders 200. A pressure sensor 110 can sense a patient condition and provide feedback or information relating to the patient condition to a microcontroller. Simply by way of example, the pressure sensor 110 can be used to detect changing limb volume or diameter, for example, such as that arising from edema, and/or to detect pressure characteristics such as might represent arterial disease or other patient characteristics. The illustrated assembly also includes an air pump or other fluid supply 126 coupled to the fluid lines 122 and 124 through respective electrically actuated fluidic solenoid valves 128 and 130 for controlling the bladders 200. The solenoid valves are controlled by one or more of the microcontrollers 116 and/or 118 through the communications or input-output component 114, and the air pump 126 is similarly controlled. The components in the assembly 100 are powered or energized by one or more batteries 132, which may be rechargeable, replaceable or otherwise controllable as desired. The additional microcontroller 118 (or suitable digital, analog and combinational circuitry) may be included to oversee the operation of the control microcontroller 116 to alert the user of possible malfunction and to shut down its operation and exhaust all pressures from the various bladders if indications so warrant.

Generally, assemblies 100A, 100B, 100C, and 100D described herein are identical, except for possibly the bladders and securements for the respective assembly based on the intended part of the body on which the assembly is to be secured. Whether or not a given assembly is coupled to a bladder will depend on the intended application, or whether or not a given assembly coupled to a bladder is used to apply pressure will also depend on the intended application. If a bladder or bladders of an assembly are not used for therapy, other components of the assembly can still be used for their intended functions, for example sensing. Additionally, assembly 100' can be identical to the assemblies 100A-100D, and can be used as a sensor, controller and/or therapy application device, depending on its intended use at the time. When used as a therapy application device, the assembly 100' can control one or more bladders by tubing (not shown) with its own pressurization apparatus, or wirelessly with pressurization apparatus associated with separate bladders. When not being used as a therapy application device, the assembly 100' can be used as a sensing assembly and/or control assembly. Alternatively, the assembly 100' can be configured to omit the pressurization apparatus, for example air pump, solenoid valves and pressure sensors and tubing.

In one form of the apparatus, the apparatus is intended to allow for ambulation of the user and is therefore self contained with an energy source such as batteries 132. During ambulation and depending in part on the therapy being applied and the location of the applied therapy, the therapy can be reduced or terminated, which can conserve energy. For example, with a venous compression device for venous insufficiency, ambulation may be an acceptable therapy, in which case other active therapy can be reduced or discontinued, thereby conserving energy.

Therapy or therapy application devices, for example bladders, are intended to be affixed to the body part. This can be accomplished in a variety of ways. One way is to position a bladder over a particular area of a body part such as an ulcerated area of skin. The bladder may have suitable wound bandage material on its exterior for direct contact with the wound or the bladder may be placed over bandages that are first applied. The bladder is then held in place using separate devices such as bands, straps, elastic stockings, hook and loop type devices such as wraps made of short stretch materials, Circaid® devices, elastic bandages (Ace), short stretch bandages or any combination of these or other holding means suitable under the circumstances, whether elastic or otherwise. Optionally, the bladder may be integral to a structure that wraps around the body part. Such a wrap can be made of materials with various stress strain characteristics which may or may not apply static pressures of various amounts of their own depending upon the stress-strain characteristics or "stretch" of the material. With a suitable minimum static pressure applied by the wrap, the bladder need only be pressurized when the wrap produces less than its originally applied pressure or when the internal hydrostatic pressure (IHP) is estimated to increase due to postural changes and a pressure greater than the minimum applied by the wrap is beneficial. Optionally the device may be applied over a wrap, elastic bandage or stocking which applies its own pressure profile and whose applied pressures are in addition to that which is applied by the device.

In one example of a therapy or therapy application device (FIG. 6), including ones that can be applied to a limb such as the calf 102 or the thigh 104 as illustrated in FIG. 1 in association with the respective assemblies 100, a compression assembly includes a compression wrap 202, a fluid bladder 204, a control unit in the form of assembly 100 (which can be any such as 100A, 1006, 100C, 100D), and securement elements, in the present example adjustment tab(s) 208 and attachment components 210 and 212 (in this case, hook and loop tape). The bladder 204 communicates fluid with the control unit through one or more communication ports 214 or through tubes (not shown) attached to and allowing fluid flow between the bladder and the control unit. In the present example, the control unit is intended to have its long axis oriented in the same direction as the tibia which ensures that the internal accelerometer is so oriented in a known fashion, as indicated at 100+, which is accomplished by placing the securement elements around a portion of the calf. The substrate material is a relatively non-stretch fabric suitable to hold reliably the bladder, the control unit and the attachment component. The adjustment tab(s) are made of fabrics that may be selected for having varying amounts of stretch. For example the tabs may have little to no stretch as does the substrate such that when applied to the patient's limb the user has less opportunity to apply a separate pressure by way of applying the wrap, which may not be as easily quantifiable. Alternatively, the tabs may have considerably more stretch such that when applied to the patient's limb the wrap applies some level of compression. The wrap is applied to the limb in the desired location, which may be a function of the therapy to be applied and the geometry of the assembly.

After the wrap is applied to the limb, the control unit is turned on. The control unit determines either that it is a dedicated unit for a particular body part, and therefore defaults to position information associated with such body part, or accepts input indicating its location on the patient. The control unit otherwise operates on default information or accepts additional input for determining the appropriate therapy to be applied as a function of time. The internal accelerometer determines the position/orientation of the limb and estimates the IHP based solely on its own data corresponding to its position sensing apparatus, or based on its own data and data from other devices, for example other position sensing devices, control units, the user or clinician, and the like. The internal fluid pump then pressurizes the bladder to the pressure appropriate to the estimated IHP using the internal pressure sensor (for example pressure sensors 110 represented in FIG. 2). A single or multiple communicating ports or tubes may be used. With multiple ports the internal pressure sensor communicates with one port while fluid input and output are communicated through another port. With a single communication port, fluid is introduced or exhausted in small increments with pressure measurements made after each increment to determine if further fluid introductions or exhaustions are needed to reach the target pressure.

In one example configuration and operation, for example for treating chronic venous disease, one possible configuration of the device is able to apply pressures as a function of IHP such that as the limb changes position, the IHP estimation is changed, the pressure in the bladder is adjusted by either allowing the pump to introduce more fluid to the bladder or the internal valve allows fluid to exhaust from the bladder. When ambulation is detected the device may prevent any fluid exchange into or out of the bladders so that muscle contractions will create increased pressure peaks that are helpful in emptying the underlying vasculature. Such emptying increases the per centage of vessel fluid volume flowing from the body part or limb. Another configuration of the device that may be used for prevention of DVT, for example, will provide cycling pressures dependent upon estimated IHP and exercise.

In another example of a therapy or therapy application device (FIG. 7), a compression assembly 222 similar to that in FIG. 6 has compression apparatus in the form of an elastic compression stocking 224 and a bladder 226 for applying pressure and/or compression. The elastic compression stocking encircles the limb, and the bladder is applied to the desired location on the limb. The bladder may be circumferential to the limb perhaps even with some overlap or it may be partially circumferential as shown. The bladder 226 may be integral to the stocking or may be a separate component that is applied first to the limb followed by the stocking. A separate bladder may be held in place in a variety of ways including adhesive, straps, or any of the other securements or holding means described herein, etc. If the control unit assembly 228 is to be supported by the limb on the compression assembly or adjacent thereto, the control unit assembly may be applied to the limb after the bladder and stocking are applied. In the present example, the control unit has its long axis oriented in the same direction as the tibia which ensures that the internal accelerometer is so oriented or otherwise in a known orientation. It can communicate fluid to the bladder through fluid port(s) 230 or through tubings 232 as shown. The control unit may be equivalent to any of the assemblies 100 described herein. The control unit in both FIGS. 6 and 7 may have controls the patient can use to turn the device on and off, for example on/off switch 234, and may also contain tactile, audible and/or visual indicators indicated schematically at 236 to communicate to the patient such things as operational status (on or off), battery life, alarm conditions of over pressure or underpressure, and/or other undesirable control changes. Tactile indications also or alternatively may be provided by using the internal fluid pump that is energized in an on-and-off pattern while the fluid is not channeled to bladder. Alternatively, tactile indications may be provided by vibrational components as found in many other devices such as mobile phones. The configuration in FIG. 7 may be used in the various treatment modes described herein as is the case with that of FIG. 6. Instead of a compression stocking, the apparatus illustrated in FIG. 7 may be secured to the leg by securements such as those described with respect to FIG. 6. The securement can be a single wrap extending along and around the calf to the area of the ankle, multiple wraps with the same extent, or individual spaced apart wraps.

Figure 8:
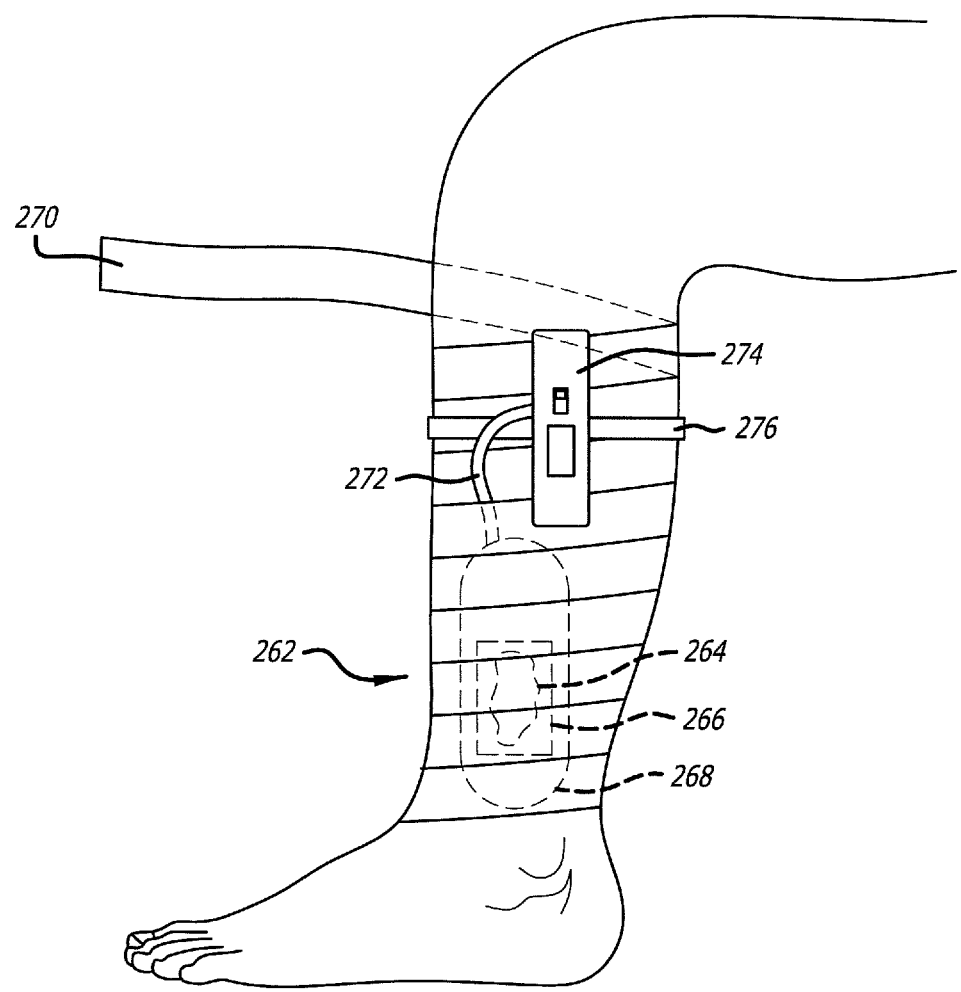
FIG. 8 is a schematic and side elevation of a bandage, for example a compression bandage, combined with a pressure or compression unit and sensor and/or control unit.

In another example of a therapy or therapy application device (FIG. 8), a compression assembly may include compression bandaging 262, for example for treating a venous ulcer 264. In the present example, a sterile dressing 266 is applied as is done in common practice. A bladder 268 is then applied over the sterile dressing and may be held in place using adhesive, straps, or other holding means as described herein, etc. In the case of using adhesive, there may be a length of double sided adhesive tape (not shown) pre-applied to the bladder whereby the release paper is removed before adhering the bladder to the dressing. A compression bandage or bandages 270 of types commonly used is/are then applied over the bladder with allowance for the bladder tubing 272 to exit through one of the overlaid wrappings of the compression bandage. A control unit 274 is then attached to the limb, for example by straps 276, a bandage layer, or other securement elements, over the compression bandage in ways similar to those described above. The control unit may be equivalent to any of the assemblies 100 described herein. The tubing 272 from the bladder is then attached to the control unit 274. In the present example, the control unit has its long axis oriented in the same direction as the tibia which ensures that the internal accelerometer is so oriented as desired or otherwise in a known orientation. The device then functions to maintain bladder pressures consistent with the estimated IHP, such as based on postural position, pressure sensing or other means, even as the compression bandage may relax over time or shift on the limb, which may otherwise reduce the intended pressure.

In any of the foregoing examples of therapy application devices, the therapy application structures can be physically separate from the patient condition sensor, for example separate from a position sensing and/or control device or devices, and if the control device is physically separate from the therapy application device, control signals can be communicated from the control unit assembly 204 to the therapy application device, or multiple therapy application devices using appropriate communications technology. If the patient condition sensing device is physically separate from the control device, patient condition data such as position or motion data can be hardwired to or communicated wirelessly or otherwise between the sensing device and the control device. The therapy application device is positioned as desired, and one or more patient condition sensing devices are reliably secured and oriented at the desired locations. Patient condition data is communicated between the sensing device and the control device, and the control device applies or sends control signals to the therapy application device for applying the therapy as desired.

Elastic stockings often lose some of their compression with wear and after washing. A patient condition sensor can be used to sense the condition or change in condition of the patient wearing an elastic stocking, for example sensing a pressure associated with a bladder under a stocking and providing information about the condition to a device, controller, therapy application device or other apparatus such as those described herein. Exemplary therapy application devices, with a bladder placed between the stocking and body part, can be used to automatically or controllably maintain the prescribed pressure as the stocking relaxes its pressure. For example, pressure sensors in fluid lines associated with the bladder can measure the pressure applied by the stockings surrounding the bladder, and as the sensed pressure decreases over the lifetime of the stocking, the setting for the pressure to be applied by the bladder can be increased accordingly. Longer stocking life and effective treatment can therefore be achieved.

These inventions also can be used to automatically or controllably maintain a prescribed pressure even if the limb geometry changes. For example, the geometry of a leg evidencing edema may change over time, such as a decrease in volume or diameter with a reduction in edema. A patient condition sensor can be used to sense the condition or change in condition of the patient, for example sensing the geometry, volume or diameter of the limb and providing information about such condition to a device, controller, therapy application device, or other apparatus such as those described herein. For example, pressure sensors associated with a bladder or other pressure application or compression device such as represented in devices 100 and 200 can be used to indicate the pressure in the fluid system for the bladder (for example such bladder 210, 226 or 268), such as when the bladder is placed on a body part. If the system is to apply a pressure of 30 mmHg but the pressure sensors indicate for the intended pressure that the actual pressure is less than 30 mmHg, feedback can be used to increase the applied pressure to the desired setting. Other conditions may cause changes in geometry, which changes can be taken into account by systems such as those described herein to adjust a therapy, for example compression or application of pressure.

With stiffer types of wraps such as short stretch bandages and Circaid type devices, ambulation may cause a lessening of applied pressure over certain portions of the body part such as the location of an ulcer. This is due to muscle contraction that moves the muscle mass away from the ulcer. With less muscle underlying the wrap at the ulcer location, pressure over the ulcer from the wrap will be diminished.

With the bladder placed over the ulcer and ambulation detected, such as by way of an accelerometer in a sensor, or by a pressure sensor as described herein, the bladder can be inflated dynamically according to the walking cycle to create a more constant pressure or a more beneficial dynamic pressure.

Bladders used in therapy or therapy application devices may have various geometries. One such bladder geometry approximates the size and shape of a typical venous ulcer. Another geometry has the bladder partially encircling a limb while yet another geometry has the bladder completely encircling the limb. Yet another geometry has the bladder surrounding an ulcerated or damaged skin area but the bladder does not cover that skin area, even though a bandage might nonetheless cover the skin area.

Patient condition sensing apparatus may include apparatus for sensing position or posture of the patient. Using position sensing apparatus as described herein, position or posture including ambulation of a body part such as an upper or lower extremity is determined by one or more position sensors, for example accelerometers, magnetometers, tilt, inclination sensors, etc., placed within the device affixed on the body part and aligned with or positioned in a known orientation relative to the body part. Typically, accelerometers are semiconductor components that are bonded to a printed circuit board as are most other electronic components. The circuit board is held within a housing in a fixed position relative to a reference point visible or known to the user or technician. The accelerometer has one or more axes of measurement, and the device can use any one or more of the axes for sensing and analysis. The axis or axes are oriented to the circuit board and therefore to the housing. In one example, the housing is then applied to the body part such that an accelerometer axis is aligned with an axis of the body part. Alternatively, the user can provide an input representing a baseline position/orientation, for example supine or prone along with the location or locations of position sensing devices on the patient. The feedback signal (s) from accelerometer(s) or the like, used singularly or in combination, are used to determine body position or posture, including information indicating ambulation, for example using information relative to the known axis aligned with the body part. Feedback signals may be used to distinguish between sitting, standing, reclining, and supine or prone. Feedback signals may also be used further to distinguish supine versus prone, for example in an accelerometer using signals associated with a second, perpendicular axis, such as perpendicular to the body part. The feedback signal(s) from accelerometer(s) or the like, used singularly or in combination, may also be used to determine body motion, such as ambulation.

Figure 3A:
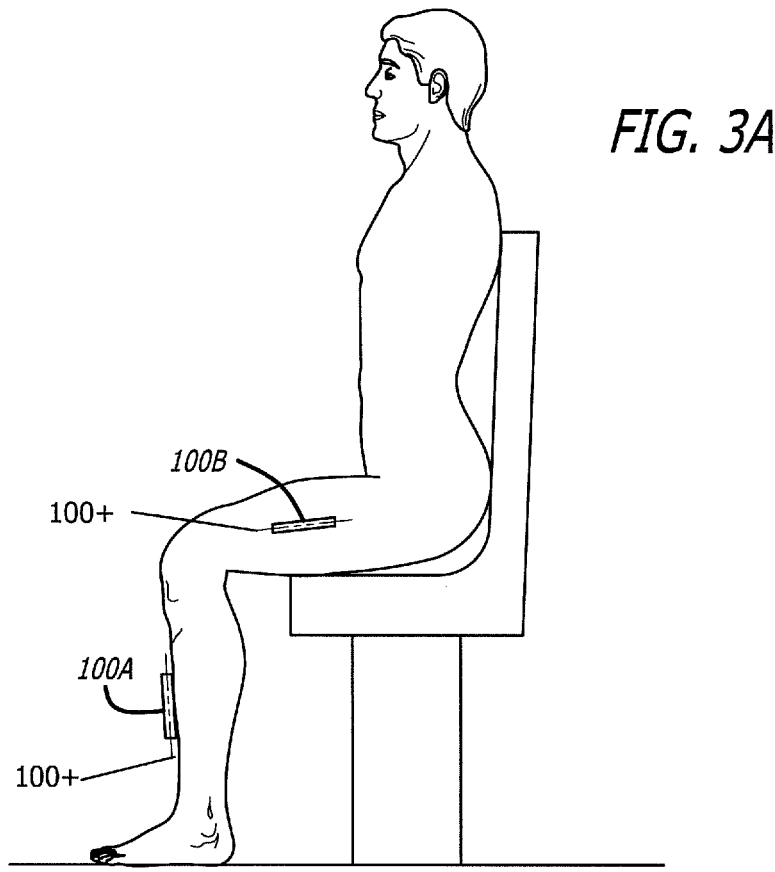
FIG. 3A is a schematic and side elevation view of a user in a sitting position with two sensor components that can be used to obtain information about the user's anatomy position or posture including ambulation.

In one example for positioning the assembly, the long axis of the assembly (represented by the dashed lines 100+ in the assemblies in FIGS. 3-5) may be aligned with the tibia bone of the lower leg or with the femur or the upper leg. The assembly is held in place using any of a variety of attachment mechanisms such as straps, temporary adhesives, hook and loop attachment straps, etc. The bladder and assembly communicate with a fluid conduit. The assembly 100 may be attached to the bladder that is held to the body part using hook and loop attachments that wrap at least partially around the body part and are connected to the bladder.

The output of the accelerometer is 0 to 1 g in a static body part with 1 g output when the limb is oriented toward the earth's center or parallel to the direction of force of gravity and 0 g when the limb is perpendicular to that direction.

In a stationary person the internal hydrostatic pressure (IHP) at a location on the limb is considered to be the vertical distance (h, in cm) from the right atrium, RA, (identifiable in practice as the level of the fourth intercostal space) to the location on the limb multiplied by the density of fluid (d) within the limb's vessels (1.06 g/cm$^3$) multiplied by 1 g where g is the gravitational acceleration of earth. Therefore, IHP=d×g×h. Another way to calculate IHP is by multiplying 0.77 mmHg/cm by the vertical distance in centimeters from the RA to the point of interest on the limb. The vertical distance can be estimated by first estimating the person's body position or posture, and if desired with knowledge of the person's height or distance from the right atrium to the point of interest on the limb. For example, with the limb segment of knee to ankle (lower leg) in a vertical position the person may be sitting or standing with vertical distances consistent with those possible positions or postures (compare FIGS. 1 and 3A). With a single assembly 100A on the calf 102 of the patient, the system has a measure of information that places the compression bladder some distance below the heart, the magnitude of which distance can be estimated within a broad range. With the limb segment from knee to hip (upper leg) in a horizontal position, and a position sensor 100B on the thigh, the person can then be estimated to be in the sitting position (FIG. 3A) with a more precisely estimated vertical distance from the heart to the compression bladder, which in the present example is approximately the same as to the center of the assembly. In another example, with the lower leg in a vertical position and upper leg in a vertical position (for example as illustrated in FIG. 1 with respective assemblies 100A and 100B), the person can be estimated to be in a standing position or posture with an associated near maximal vertical distance for that person. In another example where the person has assemblies 100A and 1006, with both upper and lower legs in a horizontal (0 g) position, the vertical distance can be estimated to be close to zero (FIG. 4A) within a given range of uncertainty, or the vertical distance can be more accurately estimated using position sensor such as an accelerometer in an assembly 100C placed and aligned on the torso (FIG. 4B), so that any range of uncertainty is narrower or reduced. When accelerometers are included in patient condition sensors, such as in assemblies 100A, 100B, 100C and 100D or 100', and their assemblies are placed as in FIG. 5 and with a single bladder on the lower leg, the vertical distance (h) from the heart to the bladder's midlevel and therefore IHP and therefore pressure in the bladder can be more accurately estimated.

Components of the position sensing device and therapy or therapy application device may include a power source, a fluid pump, one or more patient condition sensing devices, for example accelerometers or other position sensing devices, one or more pressure sensors in communication with a consistent number of bladders whose pressure is determined by the amount of fluid applied to them, valves that channel fluid from the pump to the bladders or that allow release of fluid (and pressure) from the bladders and fluid conduits that communicates fluid to the various components. Also included is a control circuit such as a microcontroller and associated software that estimates internal hydrostatic pressure and controls bladder pressures based thereon. A user or clinician may provide the patient's height or other linear measurement such as the distance from RA to the point of interest on the limb such as the location of a venous ulcer, etc., as an input to the control circuit that is used in calculating the IHP. Other possible inputs include desired pressures to be applied with various postural positions detected, such as illustrated in the examples set out in Table 1 above, or the desired increase of pressure from supine to sitting and standing. The control circuit may also vary bladder pressures as a function of time. For example, in preventing DVT the pressure may cycle from a very low pressure in the range of 0 to 20 mmHg then up to the range of 30 to 70 mmHg with the duration of lower pressures to be in the range of 30 to 60 seconds and the duration of higher pressures to be in the range of 5 to 15 seconds. These pressures may be varied according to postural position with higher pressures applied with limb dependence and lower pressures applied with supine or prone postural positions, for example using the adjustments described herein.

Activity, for example ambulation, is estimated by measuring the time rate of changes in positions or postures of body parts in addition to their direction of motion. Ambulation is inferred by a patient condition sensing device when limb motion approximates that of walking. Ambulation is detected by the use of feedback sensors, for example motion detecting and pressure transducers, and the time variance in the outputs of said transducers. Depending upon the activity measured, the device may apply more (for example more pressure for a venous ulcer during ambulation after sitting) or less pressure (for example less pressure for chronic venous disease during ambulation after sitting) and at varying timing cycles which may include applying no pressure. This can serve to save stored energy within a wearable device.

In other configurations, an assembly having a patient condition sensing apparatus and control unit apparatus may be a standalone unit with communications capabilities for controlling a therapy application device, which communications capabilities may be wired or wireless communications. In one example, such as with any of the devices 100A-100D, the assembly of patient condition sensing apparatus and control unit apparatus can have any of the position or posture sensing devices and/or patient physiological condition sensing devices described herein combined with one or more microcontrollers, signal conditioning devices, energy supply, and or other devices to provide the desired functions.

Figure 4A:
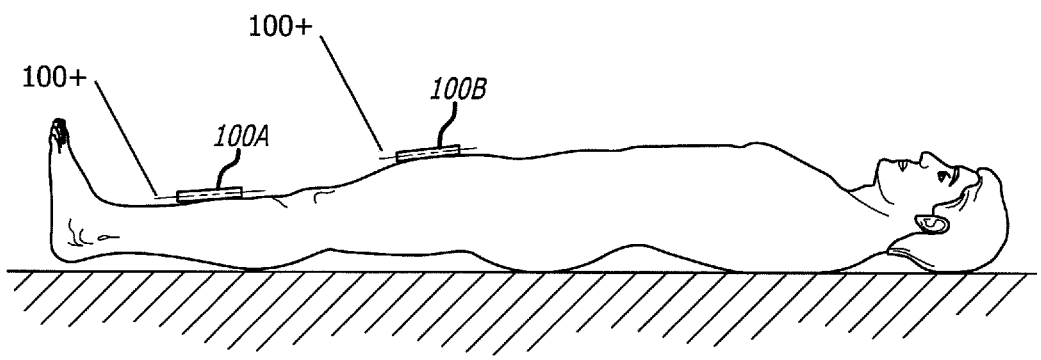
FIG. 4A is a schematic and side elevation view of a user in a supine position with two sensor components that can be used singularly or in conjunction to obtain information about the user's anatomy position or posture including ambulation.
Figure 4B:
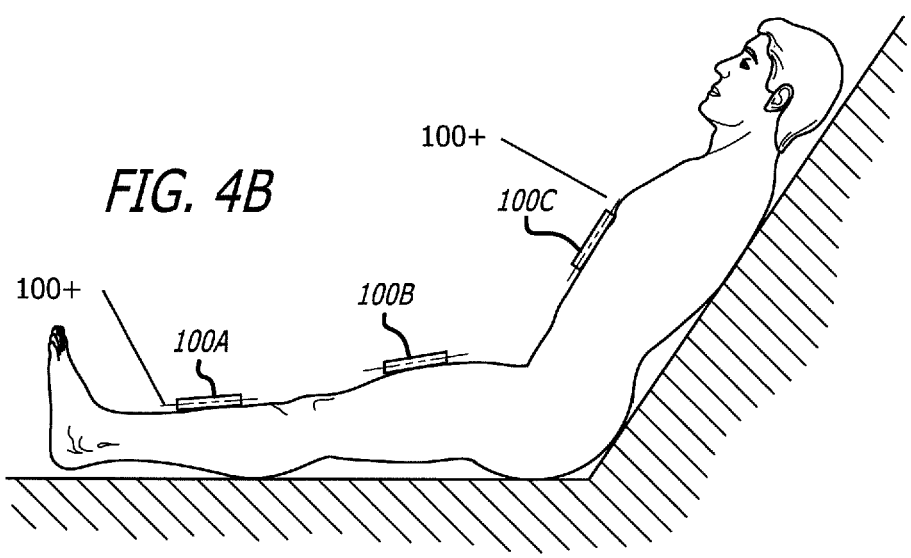
FIG. 4B is a schematic and side elevation view of a user in a reclined position with three sensor components that can be used to obtain information about the user's anatomy position or posture including ambulation.
Figure 4C:
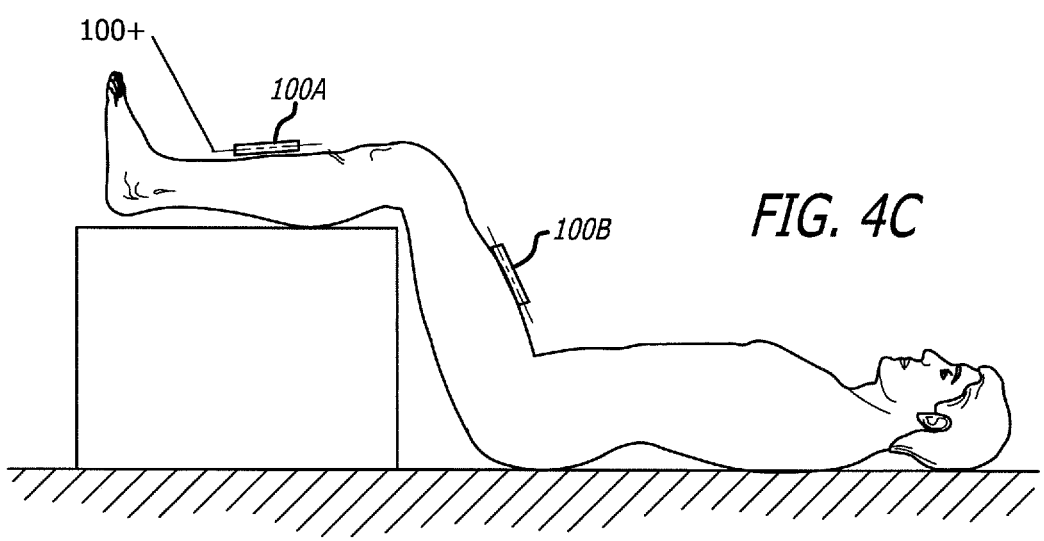
FIG. 4C is a side elevation view of a user supine and showing the lower legs raised above the torso.
Figure 4D:
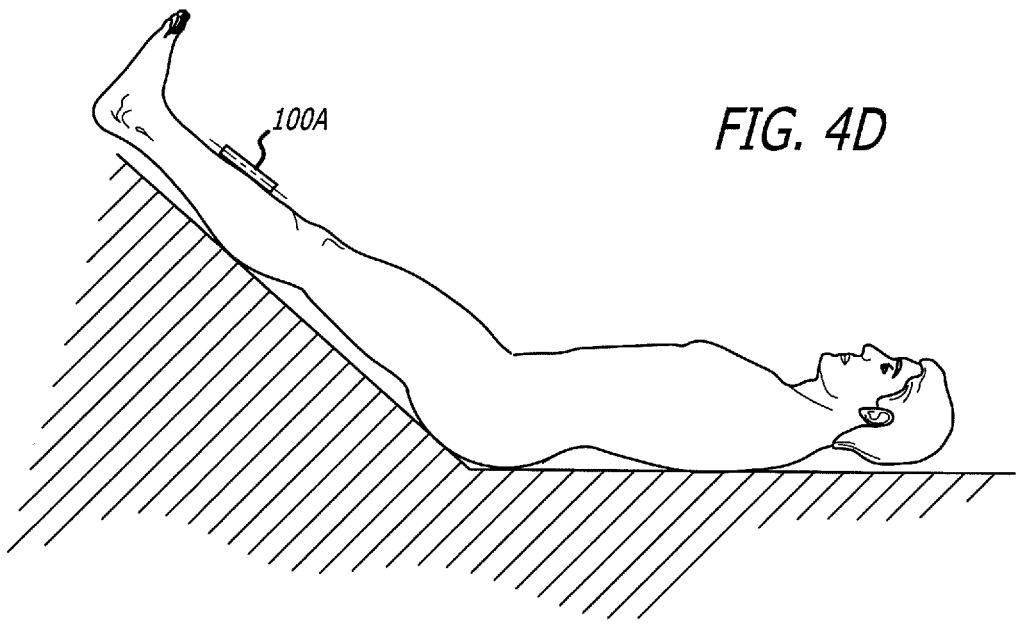
FIG. 4D is a side elevation view of a user supine and showing the legs raised above the torso and extending straight.
Figure 5:
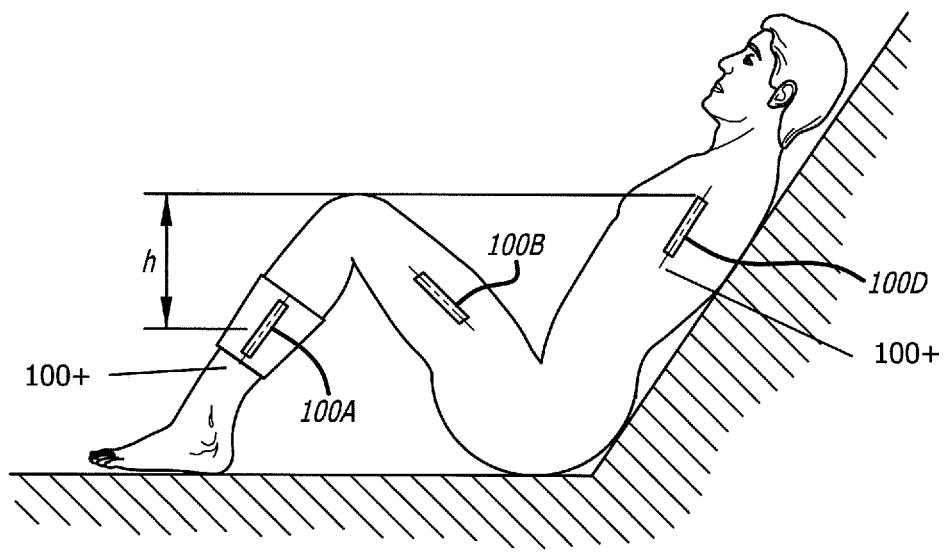
FIG. 5 is a schematic and side elevation view of a user in a reclined position with knees raised with three sensor components that can be used to obtain information about the user's anatomy position or posture including ambulation.

Position sensors are commonly available as semiconductor accelerometers, goniometers that measure the angle between body parts such as the angle at the knee, and with force sensors. Per the latter, position or posture including ambulation of the person may also be determined by adding a force sensor (i.e. strain gauge) to the plantar surface of the foot. A force closely associated to the person's weight indicates a standing position or posture, possibly including ambulation when combined with other information such as timing information, while a relatively low force indicates a sitting person, and an even lower or zero force indicating reclining (FIG. 4B) or supine positions (FIG. 4A). Such a force sensor may be affixed to the foot or placed within or on the person's shoe. Force sensing can also be accomplished by placing a bladder on the foot and measuring the pressures within it with a pressure sensor.

Therapy application devices can be configured or included within other devices for many purposes including but not limited to use for such conditions as:

Prevention of deep vein thrombosis
Treatment of chronic venous disease and sequelae
Treatment of chronic venous disease in those with arterial disease
Treatment of arterial disease
Treatment of lymphatic disease
Treatment of lipidemia
Vein enlargement and maturation
Pressure off-loading Patient condition sensing devices and the information therefrom can be used to control therapy application devices as a function of the information provided by the patient condition sensing devices. Additional examples are provided below in which information from patient condition sensing devices is used to control or modify therapy or therapy application devices.

Chronic Venous Disease

In the case of the device with only one bladder and assembly combination configured to treat chronic venous disease and its sequelae such as venous ulcers, there may be various embodiments. In one such embodiment, the pressure bladders are affixed to the control assembly 100A and affixed to the limb at the calf 102 using a hook and loop type of attachment. Bladder pressure is preset to a minimum pressure and when the patient position or posture is estimated to be either sitting or standing or established by user input, the device applies a higher pressure considered to be the IHP between those positions or postures. In another embodiment, the patient's overall height or height from the bladder to the heart may be input to provide for IHP calculation, or a default value can be used. In another embodiment, the patient may be able to manually adjust the pressure to override the preset and estimated pressure settings. The adjustment may be made in pressure units such as mmHg or as position or posture, or ambulation identifiers such as "sitting," "standing," "walking", etc., with default pressure values programmed for each condition. Table 1 is an example of patient condition presets and adjustments.

For treating chronic venous disease, a default pressure of 30 mmHg may be suitable for detected supine or prone positions while 50 mmHg may be suitable for detected sitting positions and 70 mmHg may be suitable for a detected standing position, or as shown within the above Table 1. In the case of a single accelerometer placed on the lower leg, such as on the calf 102 in FIG. 1, the device may be unable to easily and definitively discriminate between sitting and standing so a default pressure between pressures corresponding to those conditions such as 60 mmHg may be suitable. These pressure values are approximate and meant to serve as examples. The values may be changed as more is learned about the proper treatment of this disease.

In an example of a patient condition sensing apparatus, a single multi-axis accelerometer may be used with the device and placed on the lower leg.

Figure 3B:
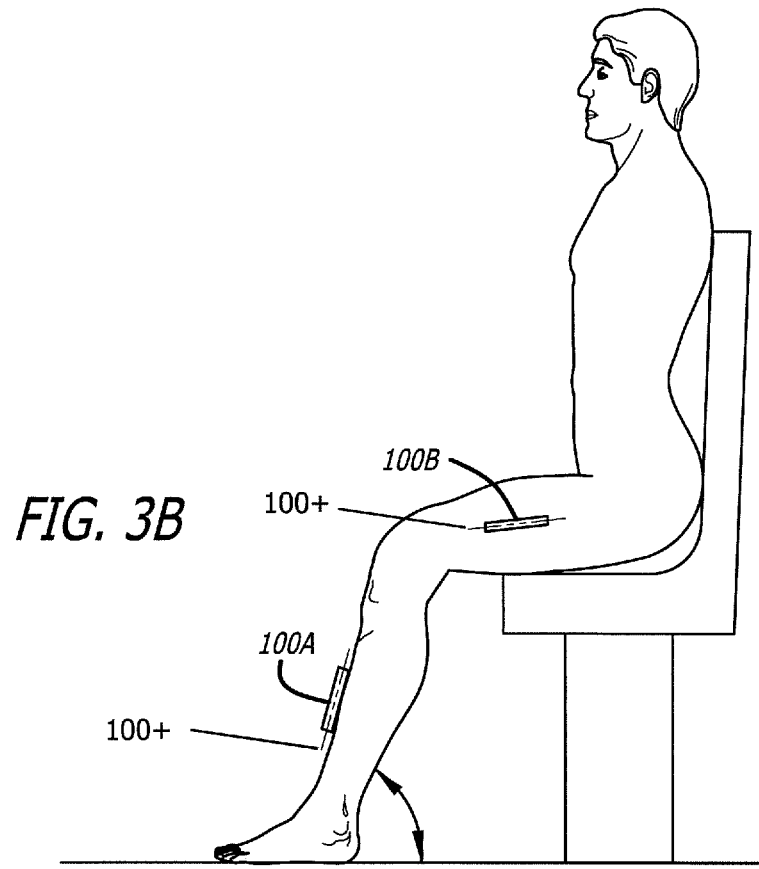
FIG. 3B is a side elevation view of a user showing the lower legs forming a non-90 degree angle to the floor.

It may be able to discriminate between sitting and standing when the angle of the lower leg is other than 90 degrees to the floor as in FIGS. 3B and 3C. This is because standing creates a 90 degree angle between the lower leg and floor. Often, people sit with their lower legs at other than 90 degrees to the floor as is the case in standing. The device's accelerometer can detect these angles and infer sitting versus standing positions and apply the appropriate pressures. The device's pressure sensor can help in determining sitting versus standing in two ways. First, muscle contractions occurring with the limb near 90 degrees to the floor will imply standing since muscles are typically more relaxed while sitting and would not be contracting as they would if the patient were standing. Second, when a person moves from the sitting to standing position, the IHP in the legs increases which causes filling of the leg veins and therefore an increase in leg volume. That increased leg volume over a relatively short period of time, the time it takes to move from sitting to standing, will cause the pressure in the bladder to increase when the pump is off and when the valves prevent bladder fluid from escaping. Additionally or alternatively, a flex sensor placed across the knee joint and fixed in position using straps or other methods may be used to discriminate between sitting and standing since a knee joint angle of 180 degrees indicates standing and an angle less than 180 degrees indicates sitting. Repeated indications of cycling between an angle of approximately 180° and an angle less than 180° would indicate ambulation.

In addition or alternative to the bladder pressure sensing functions of patient condition sensing that can be used to alter the applied therapeutic pressures described above, other ways of patient condition sensing by sensing bladder pressure may be used to alter the applied pressures, for example when arterial occlusive disease is present along with other vascular conditions such as CVI or lymphedema. Whether for use with arterial occlusive disease or for other purposes, the device described herein can also sense blood pressure as another example of sensing a patient condition. The apparatus described herein can also be used to measure blood pressure (BP) using the oscillometric method. It also can be used to measure pulse volume recordings (PVR). BP is measured when arterial pulsations are seen in the bladder whose pressure is slowly increased or decreased according to well know algorithms currently in widespread use and referred to as oscillometric methods. This device may therefore measure BP in the body part that the fluid bladder is applied to and then use that data to control the amount of applied pressure used to treat, for example, CVI or lymphedema. For example, a BP measurement could be made when the device is first applied in the supine position (FIG. 4A). This may be done, for example, to establish a baseline pressure or to determine a patient condition at the time, such as arterial occlusive disease. When the measured pressure is lower than normal it means the person also has arterial disease and the default pressures may be too high and should be reduced Also, the device could go into a "PVR" measurement mode when first applied and whenever a postural change is made. For example, when the device is applied to the limb when the patient is in the supine position, arterial pulsation amplitudes are measured, for example with a low bladder pressure of, for example, 10 mmHg. Bladder pressure is then incrementally increased in, for example, 10 mmHg increments, and the pulsation amplitudes are measured and recorded in memory for each bladder pressure. The bladder pressure or interpolated bladder pressure at which the PVR arterial pulsation amplitudes become significantly reduced may then be used to reduce the default pressure profiles. For example, if the bladder pressure at which the arterial pulsation amplitudes become significantly reduced is 30 mmHg, then the supine position's default pressure stored in the device, which may be 30 mmHg, can be reduced to a value below 30 such as 20 mmHg, or 10 mmHg less than the default setting that was selected assuming no arterial disease is present. Likewise, the sitting, standing and leg elevation (FIGS. 3A, 3B, and 3C, FIG. 1, and FIGS. 4C and 4D, respectively) pressures can each be reduced by 10 mmHg. A significant reduction in arterial pulse amplitude may be considered 10% or an amount later identified with clinical research. Importantly, the safety of the patient with arterial disease may be enhanced with some applications of the present methods during therapy.

In the example of the device measuring the BP at the bladder location, it may be used to alter the default values, for example those included in Table 1, for example by lowering them, when the BP is less than that which would be found in persons without arterial disease, for example. The difference in measured BP value from the expected normal for the patient or from the person's own brachial pressure may be used to reduce or otherwise adjust the default pressure profile values. For example, if the measured BP is 25 mmHg then the applied supine pressure may be adjusted to 25 or preferably less than 25 mmHg such as 15 or 20 mmHg. The amount of reduced pressure from the supine position's default value may then be reduced from each of the other postural position default pressure values.

Figure 9:
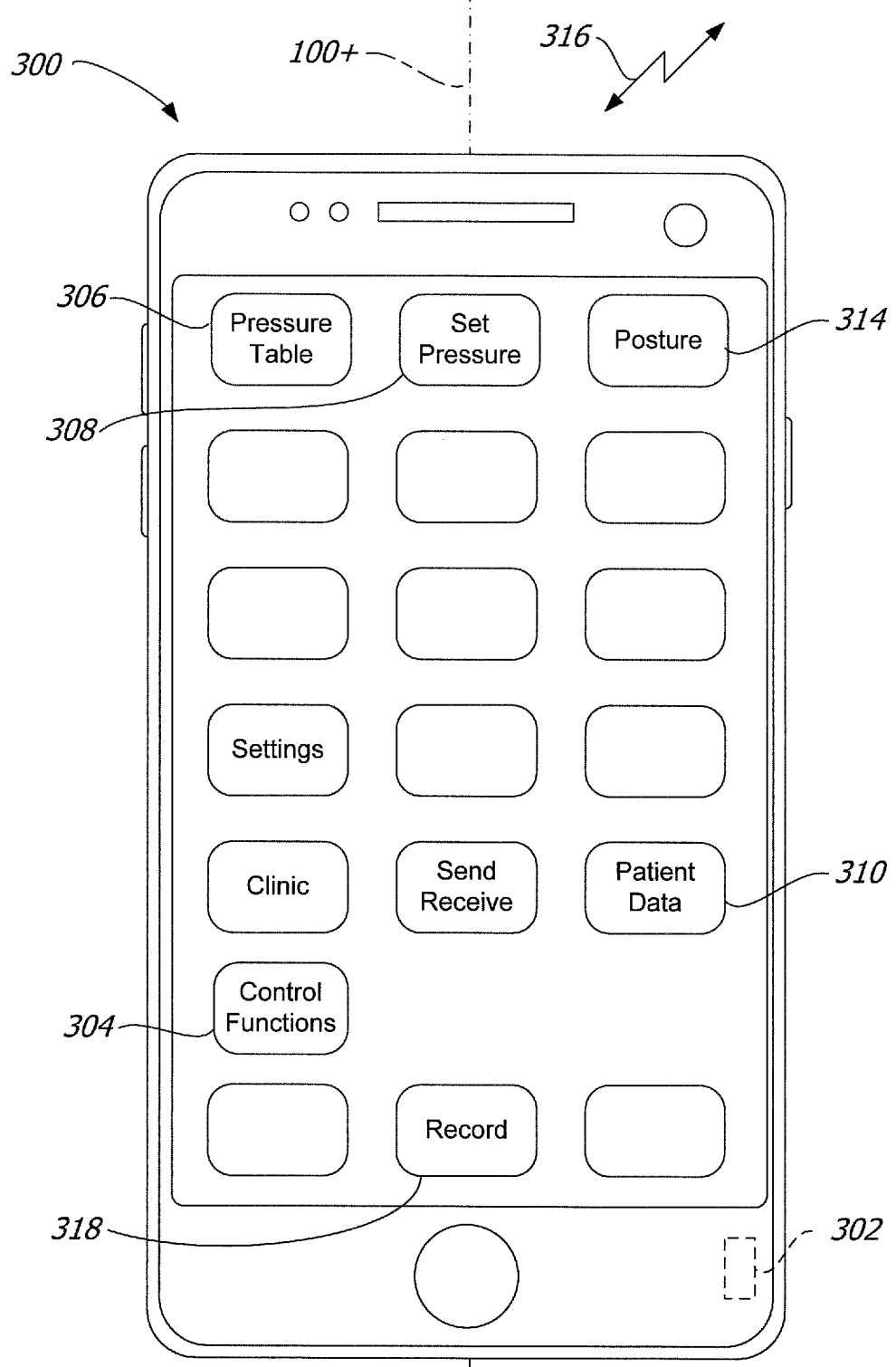
FIG. 9 is a schematic representation of a cellular telephone such as a currently common smart phone such as an iPhone X.

In another embodiment, a smart phone 300 (FIG. 9) may be used for patient condition sensing functions by way of a sensor 302 (as most smart phones incorporate an accelerometer/magnetometer), control functions 304, setting pressure values 306 and 308, setting patient biometric data 310 such as height and limb lengths used in IHP calculations, display functions 312 and for other input, for example posture or position or ambulation information 314 by the clinician and patient. The smart phone may communicate 316 with the various assemblies including those containing the pump, valve, pressure and signal conditioning functions. Either or both wired and wireless communications can be used. For those functions that use the phone's sensors 302, the phone can be affixed to the body part with a suitable holder that positions the phone in an appropriate axis, which may be represented by any of the assemblies 100A, 100B, 100C, and 100D and 100'. The smart phone may also record functional data 318 and produce it for examination by a clinician, patient or third party such as a manufacturer or distributor to evaluate the proper function, usage and health of the device.

In any of the examples described herein, including the examples of patient sensing devices, an assembly of apparatus applying therapy by inflating and/or deflating or maintaining pressure in bladders or other pressure apparatus may be separate from the patient's body. For example, an assembly containing an air pump such as air pump 126, solenoid valves such as 128 and 130, pressure sensors such as sensors 110, along with any desired electronics and communications or input output devices can be assembled separate from devices to be attached or secured to the patient's body, for example for applying therapy. For example, the apparatus can be an assembly carried by the patient, or a standalone unit such as a floor or shelf unit similar to those used in conventional compression therapies, including those used to address one or more of the patient conditions described herein. The assembly can be coupled to the desired bladder or bladders through tubing such as tubing 122 and 124 (FIG. 2), and the pressure sensors 110, in addition to their conventional functions, can be used to sense patient physiological conditions such as blood pressure and other information described herein. The assembly can have the communications and input and output apparatus and functions as desired to carry out the functions described herein, including communicating with the patient sensing devices and applying therapy to a patient using information from the patient sensing devices. Examples of separate and standalone apparatus for controlling bladders are described and illustrated in US 2011/0196269, all of which is incorporated herein by reference.

In an assembly with multiple bladders and assemblies, data or information about the positions of multiple body segments from respective patient condition sensors allow for accurate estimations of IHP as described above. Circuitry within the assemblies may communicate patient condition information, for example position or posture or ambulation data to each other using wired or wireless protocols such as Bluetooth. A single fluid pump may provide fluidized pressure to multiple bladders using flexible conduits between assemblies.

Ambulation may also be detected by sensing acceleration in other than the g axis, which is the axis that is in the direction toward the center of the Earth. When acceleration is sensed in an axis that is perpendicular to the g axis, for example, the device may infer ambulation as the leg moves, perhaps rhythmically or perhaps a measured acceleration higher than a determined threshold, in that axis during ambulation. That acceleration information may be used either alone, with pressure sensing information that identifies muscle contraction or with a flex sensor previously described as being placed across the knee joint, to further and more accurately detect ambulation and discriminate or differentiate it from standing. Additionally, identifying dynamic or rhythmic variations in the g axis value also may imply ambulation and may be used alone or in combination with the above sensing methods to help discriminate between ambulation and standing.

The device has the unique ability to treat combined venous and arterial disease since it can be programmed to apply lower pressures that would otherwise be undesirable for those with arterial disease and that have lowered perfusion pressures resulting in poor arterial perfusion. For example, after arterial or capillary perfusion pressures are measured, the device can be programmed to apply pressures that are less than the sum of perfusion pressure plus IHP. Other methods of deriving or calculating modified pressures for applying therapy can also be used.

Prevention of Deep Vein Thrombosis (DVT)

A goal of preventing DVT is the reduction of stasis. This can be achieved by applying static and/or dynamic pressures to the limb. One can make use of accelerometers to measure body position or posture including ambulation and movement in order to apply the appropriate pressures based on body position or posture including ambulation and IHP and also to improve the battery life of a self contained device that applies such pressures. An example of a therapy or therapy application device includes a DVT prevention device that can apply a static pressure whose value is adjusted based upon estimated body position or posture including ambulation as described above. A dynamic pressure, which may be separately applied or in combination with a static pressure, may also be adjusted with body position or posture including ambulation information. When using accelerometers as the patient condition sensing devices, and if they detect a dynamic pattern suggestive of ambulation, the dynamic pressures created by pump action may be temporarily halted since ambulation itself provides a muscle pump action that is preventative of DVT. This saves battery energy. Further, patient condition sensing devices such as pressure sensors in the apparatus, for example in fluid line(s) for the bladder(s), may detect pressure changes in the bladder by leaving a small or lower residual bladder pressure between dynamically applied pressures, and sensing perturbations. The pressure sensors are able to identify muscle contractions by the pressure perturbations created. During and for some period of time after muscle contractions are identified the device can temporarily halt the pump operation since muscle contraction is preventative of DVT. Pressure sensors can be used as patient condition sensing devices in any of the apparatus described herein.

In one example for prevention of DVT, default values may produce pressures that may be cycled from a lower static pressure to a higher static pressure. In one example, a lower static pressure can be in the range of 0 to 20 mmHg (in one example approximately 10 mmHg), and then the static pressure could be raised up to a pressure in the range of 30 to 70 mmHg (in one example around 50 mmHg) based on changing conditions resulting from postural changes, for example as determined by patient condition sensors. During a cycle, the duration of a lower static pressure can be in the range of 30 to 60 seconds (in one example approximately 60 seconds), and the duration of a higher pressure can be in the range of 5 to 15 seconds (in one example approximately 10 seconds). The cycle can repeat during the application of therapy, or can be changed as conditions change.

In another example, pressures can be changed as a function of a selected condition, for example a high, peak or pulsing pressure. In such an example, a high pressure can be determined, for example as a function of the user's position, and that high pressure used to set a lower static pressure, for example between 10 to 30 mmHg below the high pressure, in one example approximately 15 mmHg below the higher pressure. Alternatively, a baseline pressure can be used, selected as a function of the user's position, and the baseline pressure used to set the higher pressure. In such an example, the baseline pressure can be any of the static pressures described herein, including in Table 1, for example in the range of 0 to 20 mmHg, and the higher pressure determined by adding a pressure increment to the baseline, for example a pressure increment in the range of 20-40 mmHg, and one example adding a pressure increment of approximately 30 mmHg. In any of the foregoing cases, the timing of the lower pressure and of the higher pressure can be selected as desired, and in one example a higher pressure can have a duration in the range of between 5 and 15 seconds, in one example approximately 10 seconds and in another example approximately 12 seconds. The lower pressures can have a duration in the range of 30 to 60 seconds, and in one example approximately 60 seconds. The pressures described in the foregoing examples can be varied as a function of postural position, with higher static and greater high pressures applied with limb dependence, and lower static and lesser high pressures applied with supine or prone postural positions, for example as described in other examples herein.

The foregoing examples of determining or selecting lower and higher pressures or baseline or static and pulsing pressures for prevention of DVT can also be applied to the examples of other therapy applications identified herein, including the treatment of chronic venous disease and sequelae, treatment of arterial disease, treatment of lymphatic disease, etc. Treatment modalities can be monitored and adjusted as a function of position and positional changes.

Vein Enlargement and Maturation

Devices used for vein enlargement and maturation cyclically compress the veins proximal to the fistula. Use of the above concepts of estimating IHP and muscle movement will be beneficial in that a better compression pressure can be used and battery energy of a self contained device can be conserved. When applied to the forearm, if accelerometers or other sensors detect a vertical dependent limb (hand below elbow), the amount of pressure applied can be increased beyond that which is applied when the forearm is horizontal. A vertical limb detected with the hand above the elbow would mean that less pressure would be needed to compress the veins. When pressure sensors detect pressure perturbations within the bladder suggestive of muscle contractions, the device can temporarily halt the pump operation since muscle contractions are themselves prescribed as beneficial to vein maturation. By leaving a small residual bladder pressure between dynamically applied pressures, the pressure sensors are able to identify muscle contractions.

Pressure Off-Loading

Pressure ulcers are injuries to skin and underlying tissue resulting from prolonged pressure on the skin. They most often develop on skin that covers bony areas of the body, such as the heels, ankles, hips and tailbone. They may occur when a patient remains immobile in a bed or chair. Using a pressure ulcer on the tailbone as an example, it would be preferred to apply a higher surrounding and off-loading pressure when the patient is in a sitting or semi recumbent position (FIG. 4B) than when in a supine position. With an accelerometer containing assembly applied to the body above (cephalad to) the tailbone the device can detect the postural position, estimate the added IHP and apply a pressure consistent with that IHP.

Having thus described several exemplary implementations, it will be apparent that various alterations and modifications can be made without departing from the concepts discussed herein. Such alterations and modifications, though not expressly described above, are nonetheless intended and implied to be within the spirit and scope of the inventions. Accordingly, the foregoing description is intended to be illustrative only.

What is claimed:

1. An assembly for applying therapy by pressure to a patient as a function of a patient condition, the assembly comprising:
   a pressure therapy apparatus configured to be applied to a surface of the body of a patient;
   means for securing the pressure therapy apparatus to the surface of the patient's body;
   a patient condition sensor in the form of a position sensor and a pressure sensor wherein the patient position sensor is at least one of an accelerometer, magnetometer, gyroscope, inclination sensor, tilt sensor, goniometer, or flex sensor;
   an input element configured to receive information about a condition of the patient from the patient condition sensor; and
   a controller configured to operate the pressure therapy apparatus as a function of the information received about the condition of the patient, and as a function of a change in an internal hydrostatic pressure of the patient estimated from the information.

2. The assembly of claim 1 wherein the pressure therapy apparatus is a bladder and the securing means includes means for securing the pressure apparatus on a patient's limb.

3. The assembly of claim 1 wherein the input element includes at least one of a wireless communications device and a wired connection.

4. The assembly of claim 1 wherein the position sensor includes the accelerometer within a housing wherein the input element and the controller are supported in the housing.

5. The assembly of claim 1 wherein the pressure sensor is configured to sense fluid pressure in a fluid line coupled to the pressure therapy apparatus and provide fluid pressure data to the controller.

6. The assembly of claim 1 wherein the input element includes a user interface configured to receive information about a patient.

7. The assembly of claim 6 wherein the user interface is configured to receive information about the patient including at least one of height, weight and sex.

8. The assembly of claim 6 wherein the user interface is configured to receive information of at least one of a distance from the right atrium of the patient to a location of a pressure device, a distance from a top of the head to the right atrium or a distance from a sole of a foot to a location of a pressure device.

9. The assembly of claim 1 wherein the pressure therapy apparatus includes at least one of a compression stocking, compression bandage, compression cuff or compression boot.

10. The assembly of claim 1 wherein the means for securing the pressure therapy apparatus is configured to extend around a perimeter of a limb and a housing containing the controller has a recognizable orientation relative to the securing means and a perimeter of a limb.

11. The assembly of claim 10 wherein the housing containing the controller is in a substantially fixed orientation relative to the pressure therapy apparatus.

12. The assembly of claim 1 wherein the pressure therapy apparatus includes a bladder that is configured to extend at least partly around a patient's calf.

13. The assembly of claim 12 wherein the bladder and a housing for the controller are mounted to each other with at least one fluid port extending from the housing to the bladder.

14. The assembly of claim 12 wherein the input element is configured to sense whether the patient's calf is suspended.

15. The assembly of claim 12 wherein the input element is a first accelerometer supported by the securing means, and wherein the assembly further includes a second pressure therapy apparatus and a second accelerometer configured to be secured to a patient's thigh.

16. The assembly of claim 12 wherein the input element is the accelerometer and wherein the assembly further includes a goniometer configured to be supported on the patient's thigh.

17. An assembly for applying therapy by pressure to a patient as a function of a patient condition, the assembly comprising:
   a pressure therapy apparatus including a bladder configured to be applied to a surface of the body of a patient wherein the bladder is configured to extend at least partly around a patient's calf;

means for securing the pressure therapy apparatus to the surface of the patient's body;

an input element configured to receive information about a condition of the patient; and a controller configured to operate the pressure therapy apparatus as a function of the information received about the condition of the patient, and as a function of a change in an internal hydrostatic pressure of the patient estimated from the information; and wherein the input element is a physiological measurement sensor and at least one of an accelerometer and a goniometer secured to the patient's calf with the securing means.

18. The assembly of claim 17 wherein the pressure therapy apparatus is a first pressure therapy apparatus and further including a second pressure therapy apparatus configured to extend at least partly around a patient's thigh and wherein the second pressure therapy apparatus includes an input element that is at least one of an accelerometer and a goniometer.

19. The assembly of claim 18 wherein the input element secured to the patient's calf is an accelerometer and wherein the input element for the second pressure therapy apparatus includes a goniometer.

20. An assembly for applying therapy by pressure to a patient as a function of a patient condition, the assembly comprising:

a pressure therapy cuff, a physiological measurement sensor and an accelerometer configured to be applied to a patient's calf; and a controller configured to operate the pressure therapy cuff as a function of data from the accelerometer, and as a function of a change in an internal hydrostatic pressure of the patient estimated from the data.

21. The assembly of claim 20 further including a wireless communication device for communicating information between the controller and at least one of the pressure therapy cuff and the accelerometer.

22. The assembly of claim 20 wherein the controller includes a user interface configured to receive information about the patient including at least one of height, weight and sex.

23. The assembly of claim 20 wherein the controller is configured to receive information of at least one of a distance from the right atrium of the patient to a location of a pressure device, a distance from a top of the head to the right atrium or a distance from a soul of a foot to a location of a pressure device.

24. The assembly of claim 20 wherein the controller is associated with a housing when a housing is configured to be in a substantially fixed orientation relative to the pressure therapy cuff.

25. An assembly for applying therapy by pressure to a patient as a function of a patient condition, the assembly comprising:

a pressure therapy cuff configured to be applied to a calf of a patient;

a physiological measurement sensor;

an accelerometer configured to be supported on a calf of a patient;

a goniometer configured to be supported in a known position relative to a calf of the patient; and a controller configured to receive data from the accelerometer and from the goniometer and configured to control the pressure therapy cuff as a function of data received from at least one of the accelerometer and the goniometer, and as a function of a change in an internal hydrostatic pressure of the patient estimated from the data.

26. The assembly of claim 25 wherein the goniometer is configured to be supported on a thigh of the patient.

27. A method of applying pressure therapy to a limb of a patient comprising:

receiving in a controller input data about a condition of the patient, the condition including an estimated change in an internal hydrostatic pressure of the patient;

applying pressure to the limb of the patient as a function of the data about the condition of the patient; and wherein the input data is a physiological measurement acquired with a physiological measurement sensor and at least one of a patient position, patient posture, patient ambulation acquired with at least one of an accelerometer, magnetometer, gyroscope, inclination sensor, tilt sensor, goniometer, or flex sensor.

28. The method of claim 27 further including receiving input data in the controller and adjusting the pressure applied to the limb of the patient from a pressure associated with a patient supine position to a pressure adjusted for an estimated change in the internal hydrostatic pressure for the limb of the patient.

29. The method of claim 27 wherein applying pressure to the limb includes applying pressure to a calf of the patient.

\* \* \* \* \*